US006365364B1

(12) United States Patent
Mann et al.

(10) Patent No.: US 6,365,364 B1
(45) Date of Patent: Apr. 2, 2002

(54) ANGIOGENESIS INHIBITORS AND USES THEREOF

(75) Inventors: Kenneth G. Mann, Grand Isle; Nancy Swords Jenny, Colchester, both of VT (US)

(73) Assignee: University of Vermont and State Agriculture College, Burlington, VT (US)

( * ) Notice: Subject to any disclaimer, the term of this patent is extended or adjusted under 35 U.S.C. 154(b) by 0 days.

(21) Appl. No.: 09/377,250

(22) Filed: Aug. 19, 1999

Related U.S. Application Data

(60) Provisional application No. 60/097,244, filed on Aug. 20, 1998.

(51) Int. Cl.$^7$ .............................. C12Q 1/56; C12Q 1/00; C12N 9/99; G01N 33/574; G01N 33/53
(52) U.S. Cl. .................. 435/13; 435/184; 435/7.23; 435/7.71; 435/4; 530/380
(58) Field of Search ................... 530/380; 435/13.4, 435/7.23, 7.71; 514/2

(56) References Cited

U.S. PATENT DOCUMENTS

| | | | |
|---|---|---|---|
| 4,350,625 A | 9/1982 | Abe | 260/112 R |
| 4,709,014 A | 11/1987 | Tamaoki | |
| 5,260,060 A | 11/1993 | Markland, Jr. et al. | 424/94.67 |
| 5,637,492 A | 6/1997 | Dawson et al. | 435/217 |
| 5,639,725 A | 6/1997 | O'Reilly et al. | 514/12 |
| 5,792,845 A | 8/1998 | O'Reilly et al. | |
| 5,837,682 A | 11/1998 | Folkman et al. | |

FOREIGN PATENT DOCUMENTS

| | | |
|---|---|---|
| EP | 0 020 780 A1 | 11/1979 |
| WO | WO 80/01039 | 5/1980 |

OTHER PUBLICATIONS

Burgess et al., J of Cell Bio. 111:2129–2138, 1990.*
Lazar et al. Molecular and Cellular Biology 8:1247–1252, 1988.*
Patterson et al, 1997, Jnl.Biol.Chem, V272(14), 28823–25.*
Cao, et al., *J. of Biological Chemistry*, 271:46, 29461–29467 (1996).
Dong, et al., *Cell*, 88:801–810, (1997).
Herbert J. Evans, *Biochimica et Biophysica Acta*, 660:219–226 (1981).
Herbert J. Evans, *Biochimica et Biophysica Acta*, 802:49–54 (1984).
Evans, et al., *J. of Biological Chemistry*, 255:8, 3793–3797 (1980).
Karlsson, et al., *Biochimica et Biophysica Acta*, 127:505–520 (1996).
Kelm Jr., et al., *J. of Biological Chemistry*, 269:48, 30147–30153 (1994).
Machovich, et al., *Biochemistry*, 28:4517–4522, (1989).
Mohamed N.M. Omar, Univ. of Vermont For the Ph.D. in Biochemistry, (1986).
O'Reilly, et al., *Cell*, 79:315–328 (1994).
Stathakis, et al., *J. of Biological Chemistry*, 272:33, 20641–20645 (1997).
Mahmoud I. Hassan, Ain Shams University For the Ph.D. Degree, (1985).
J. Schmitt, et al. "Affinity Purification Of Histidine–Tagged Proteins", *Molecular Biology Reports*, Oct. 1993, vol. 18, No. 3, pp. 223–230.
Copy of Int'l Search Report dated Feb. 9, 2000, of corresponding Int'l Appln. No. PCT/US99/18877 (six pages).
Janknecht, R., et al. "Affinity Purification Of Histidine–Tagged Proteins Transiently Produced In HeLa Cells", *Gene*, vol. 121, No. 2, (1992), pp. 321–324.

\* cited by examiner

*Primary Examiner*—Anthony C. Caputa
*Assistant Examiner*—Gary B. Nickol
(74) *Attorney, Agent, or Firm*—David G. Conlin; Robert L. Buchanan; Edwards & Angell, LLP

(57) ABSTRACT

The present invention features isolated angiogenesis inhibitors having a molecular weight of between about 40 kDa to 50 kDa and having an amino acid sequence substantially similar to that of the amino acid sequence shown in SEQ ID NO. 2 or SEQ ID NO. 3. Further provided are methods of making and using the angiogenesis inhibitors, e.g., to inhibit vascularization or to block osteonectin and plasminogen interaction.

7 Claims, 10 Drawing Sheets

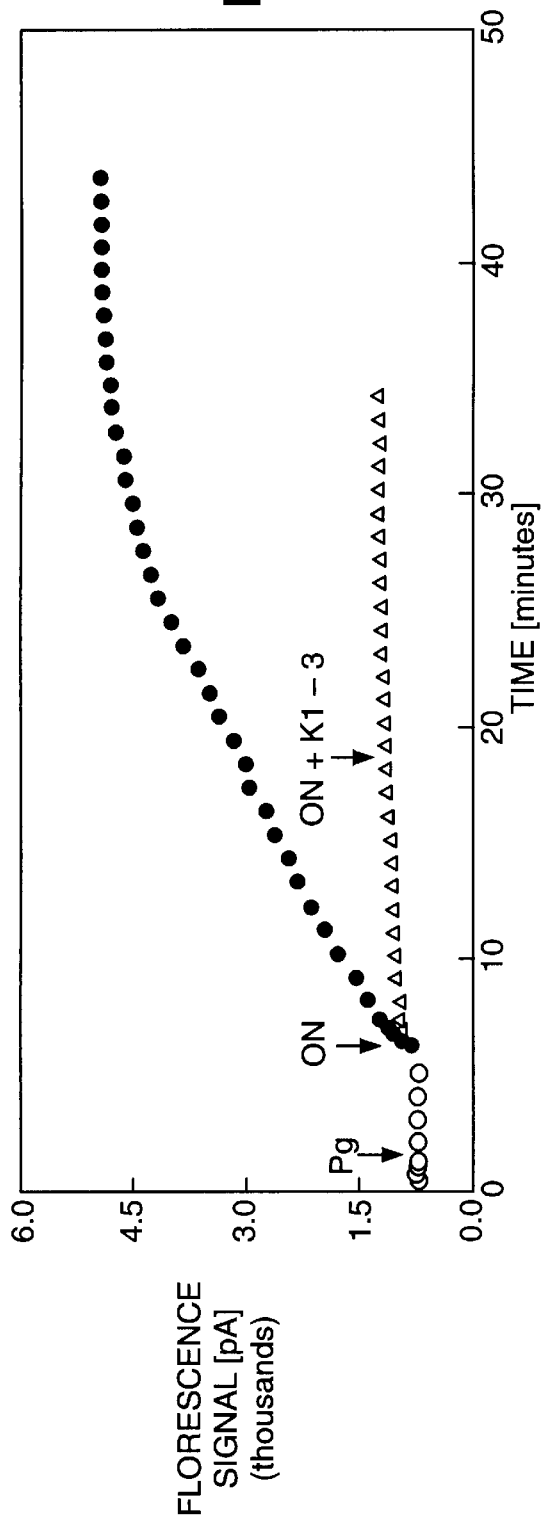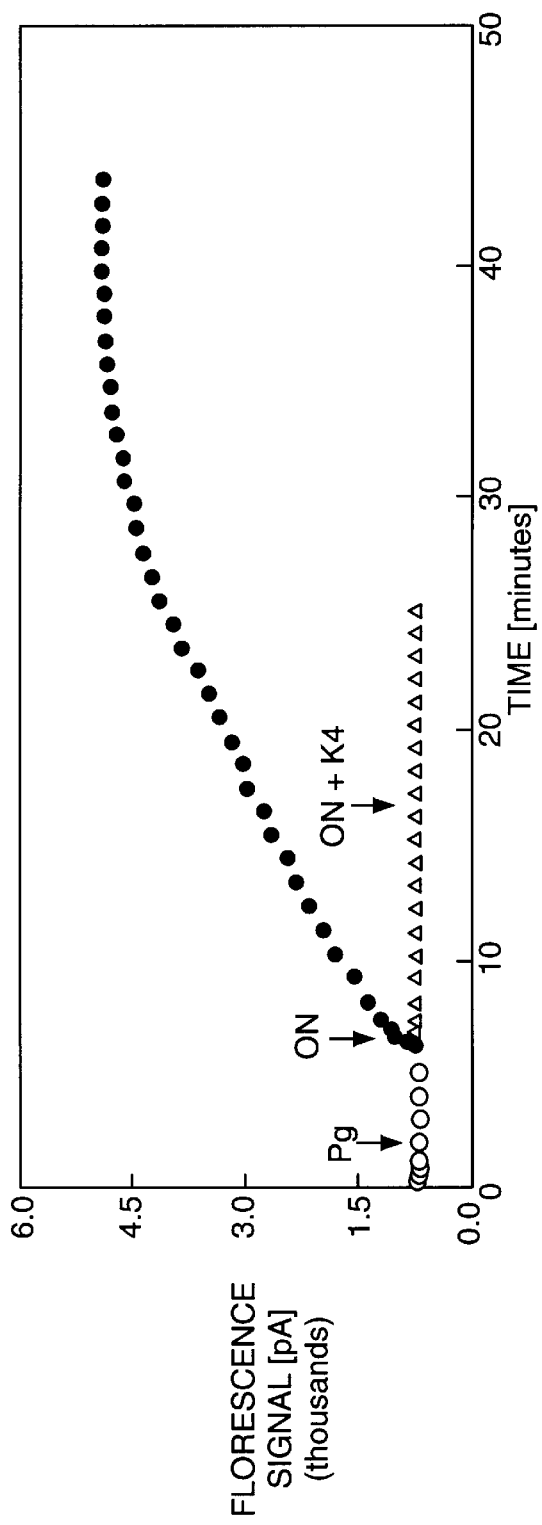

Sequence ID No 1, residues 1-451/452

NH₂ - EPLDDYVNTQGASLFSVTKKQLGAGSIEECAAKC
EEDEEFTCRAFQYHSKEQQ/ECVIMAENRKSSII(I)RMR
DVVLFEKKVYLSECKTGNGKNYRGTMSKTKNGITCQ
KWSSTSPHRPRFSPATHPSEGLEENYCRNPDNDPQGP
WCYTTDPEKRYDYCDILECEEECMHCSGENYDGKIS
KTMSGLECQAWDSQSPHAHGYIPSKFPNKLKKNYC
RNPDRELRPWCFTTDPNKRWELCDIPRCTTPPPSSGP
TYQCLKGTGENYRGNVAVTVSGHTCQHWSAQTPHTH
NRTPENFPCKNLDENYCRNPDGKRAPWCHTTNSQVR
WEYCKIPSCDSSPVSTEQ/ELAPTAPPELTPVVQDCYH
GDGQSYRGTSSTTTGKKCQSWSSMTPHRHQKTPEN
YPNAGLTMNYCRNPDADKGPWCFTTDPSVRWEYCN
LKKCSGTEASVVAPPPVVLLP - COOH

FIG. 8

Sequence ID No 2, residues 77-451/452

NH₂ - KVYLSECKTGNGKNYRGTMSKTKNGITCQ
KWSSTSPHRPRFSPATHPSEGLEENYCRNPDNDPQGP
WCYTTDPEKRYDYCDILECEEECMHCSGENYDGKIS
KTMSGLECQAWDSQSPHAHGYIPSKFPNKNLKKNYC
RNPDRELRPWCFTTDPNKRWELCDIPRCTTPPPSSGP
TYQCLKGTGENYRGNVAVTVSGHTCQHWSAQTPHTH
NRTPENFPCKNLDENYCRNPDGKRAPWCHTTNSQVR
WEYCKIPSCDSSPVSTEQ/ELAPTAPPELTPVVQDCYH
GDGQSYRGTSSTTTGKKCQSWSSMTPHRHQKTPEN
YPNAGLTMNYCRNPDADKGPWCFTTDPSVRWEYCN
LKKCSGTEASVVAPPPVVLLP - COOH

FIG. 9

Sequence ID No 3, residues 78-451/452

NH₂ - VYLSECKTGNGKNYRGTMSKTKNGITCQ
KWSSTSPHRPRFSPATHPSEGLEENYCRNPDNDPQGP
WCYTTDPEKRYDYCDILECEEECMHCSGENYDGKIS
KTMSGLECQAWDSQSPHAHGYIPSKFPNKNLKKNYC
RNPDRELRPWCFTTDPNKRWELCDIPRCTTPPPSSGP
TYQCLKGTGENYRGNVAVTVSGHTCQHWSAQTPHTH
NRTPENFPCKNLDENYCRNPDGKRAPWCHTTNSQVR
WEYCKIPSCDSSPVSTEQ/ELAPTAPPELTPVVQDCYH
GDGQSYRGTSSTTTTGKKCQSWSSMTPHRHQKTPEN
YPNAGLTMNYCRNPDADKGPWCFTTDPSVRWEYCN
LKKCSGTEASVVAPPPVVLLP - COOH 451(452)

ANGIOGENESIS INHIBITORS AND USES THEREOF

This application claims benefit to provisional application 60/097,244 filed on Aug. 20, 1998, now abandoned. The disclosure of the 60/097,424 application is hereby incorporated by reference.

FIELD OF THE INVENTION

The present invention relates to inhibitors of blood vessel growth (angiogenesis) and particularly to amino acid sequences that can reduce or eliminate angiogenesis. In one aspect, the invention features methods for making angiogenesis inhibitors. The invention has a variety of applications including use in the treatment of angiogenesis-associated diseases such as cancer.

BACKGROUND

It is recognized that angiogenesis plays a role in diseases such as cancer. Therapies that can reduce or eliminate angiogenesis have been reported to be useful in the treatment of cancer and other angiogenesis-related diseases. See generally, Folkman J., (1971) *N. Engl. Jour. Med.* 285:1182; Folkman, J. (1989) *J. Natl. Cancer Inst.* 82: 4; O'Reilly, M. S. et al. (1994) *Cell*, 79: 315 and references cited therein.

There has been significant effort toward developing therapies that can reduce or eliminate angiogenesis. One approach has been to identify specific compounds that block or reduce growth of new blood vessels (neovascularization). See e.g., Ingber D, et al. (1990) *Nature*, 48:555; Clapp, C. et al. (1993) *Endocrinology* 133: 1292; and Folkman, J. (1995) *N. Engl. J Med.* 333: 1757.

Particular attention has focused on a compound called "angiostatin". This compound has been reported to be a 38 kDa to 45 kDa fragment from plasminogen. See generally O'Reilly, M. S. (1997) in: *Regulation of Angiogenesis* (I D Goldberg and E M Rosen, eds) Birkhauser Velag (Basel, Switzerland), pgs. 273–294.

Plasminogen is a protein involved in many physiological processes such as clot lysis. The protein includes five linked domains that are sometimes called "kringles". Each kringle can be referred to as K1, K2, K3, K4 and K5, respectively. The K5 kringle is fused to a plasmin domain to form what is sometimes called a B chain. See e.g., Kelm R. J. et al (1994) *J. Biol. Chem.* 269:30147 and references cited therein.

Angiostatin has been disclosed as consisting of plasminogen kringles K1–4 Nucleic acid and protein sequences for angiostatin and various plasminogens have been reported. See e.g., Cao, Y. (1996) *J. Biol. Chem.* 271:29461; O'Reilley, M. S. et al. (1994, 1997) supra; and U.S. Pat No. 5,639,725.

Specific fragments of angiostatin have been reported to have anti-angiogenic activity. Sometimes the fragments are referred to as "angiostatin-like" to denote capacity to block blood vessel growth. Examples of such fragments include the K1 and K1–3 Kringles. The K5 fragment has been reported to have minimal anti-angiogenic activity. See e.g., Cao, Y. supra.

There is increasing recognition that angiostatin is a strong inhibitor of neovascularization in vitro and in vivo. Thus, there has been an emerging need to develop effective methods for producing angiostatin and angiostatin-like fragments.

Several methods for producing angiostatin use proteases to cleave plasminogen into specific fragments. For example, one reported way to make angiostatin involves treating plasminogen with a protease called elastase. The fragments produced by the elastase are subsequently purified by conventional techniques.

However, the prior methods for making angiostatin are associated with significant problems. For example, many proteases produce disrupted kringle domains. That is, the proteases cleave plasminogen at more than one site. As a specific example, elastase has been reported to produce not only K1–4 (angiostatin) but also the K1–3 and K4 fragments. Although these methods can produce some angiostatin, isolation of significant amounts of the protein can be complicated by the other kringles. More generally, production of multiple fragments from plasminogen can substantially reduce yields and make purification of angiostatin and angiostatin-like fragments more difficult.

Additionally, many of the prior methods do not always completely remove the K5 fragment, thereby reducing the activity of certain angiostatin-like fragments.

One attempt to remedy this problem has been to minimize plasminogen cleavage. For example, one specific attempt has tried to reduce the amount of elastase used to cleave plasminogen so that larger kringle fragments can be obtained. However, this approach suffers from several drawbacks. For example, the need to reduce the amount or activity of the elastase makes assays more error prone and resistant to standardization and quality control. Use of other proteases has given rise to related problems. These shortcomings can be magnified by a variety of parameters, particularly during attempts to scale-up the methods.

The general availability of plasminogen and related molecules has supported efforts to isolate angiostatin by methods that include proteolytic cleavage. However, other approaches have been used to make angiostatin, e.g., recombinant DNA techniques. Use of the recombinant DNA techniques can be frustrated however by inability of some host cells to express suitable quantities of soluble protein. Additionally, there may be resistance to using recombinant DNA products in some settings.

It would be desirable to have angiogenesis inhibitors and more effective methods for producing same. It would be particularly desirable to have effective methods for making angiogenesis inhibitors from plasminogen that reduce or eliminate disruption of K1–4.

SUMMARY OF THE INVENTION

The present invention relates to angiogenesis inhibitors and effective methods for producing same from plasminogen. In general, we have discovered that by treating plasminogen with a specific cobra protein it is possible to enhance isolation of the angiogenesis inhibitors from plasminogen while minimizing or eliminating disruption of the first four plasminogen kringles (K1–4). The present invention has a variety of useful applications including use in the treatment of angiogenesis-associated diseases such as cancer.

In one aspect, we have found that cobra venom, particularly from the spitting cobra (*Naja Nigricollis Nigricollis*, hereinafter *Naja Nigricollis*), includes a protein and particularly a protease that is especially useful for producing certain angiogenesis inhibitors. More particularly, we have found that a protease (hereinafter "K-4 protease") found in cobra venom specifically cleaves plasminogen at a single site near the K4 and K5 kringles, thereby isolating, in a single fragment, nearly all of the K1–4 fragment. Disruption of the K1–4 fragment is reduced or eliminated by use of the K-4 protease. Additionally, we have found that use of the K-4 protease can enhance activity of the present angiogenesis inhibitors by removing the K5 fragment therefrom. Practice of the present invention can enhance the preparation and use of the angiogenesis inhibitors by significantly boosting yields of nearly intact K1–4 fragment.

In contrast to the present invention, prior methods for making anti-angiogenic compounds from plasminogen often use methods that disrupt the K1–4 fragment and do not always efficiently remove K5 therefrom. Thus, yields of intact K1–4 are often decreased by the prior methods.

FIG. 1 provides a schematic representation of human plasminogen including the plasmin catalytic domain (catalytic domain), the first five plasminogen kringles (K1–5) attached to the plasmin domain (5B chain), and the *Naja Nigricollis* (K-4) protease cleavage site.

The present angiogenesis inhibitors can be made by one or a combination of different strategies in accord with the invention. In one approach, plasminogen or other suitable plasminogen-related molecule is treated with an amount of the K-4 protease sufficient to cleave the plasminogen or related molecule at a single specific site. As will be discussed, that site has been determined to be near the border between of the K4 and K5 fragments of plasminogen. More particularly, the K-4 protease has been found to cleave plasminogen specifically between amino acid position 451 and 452. Thus, unless specified otherwise, the angiogenesis inhibitors of the invention include a C-terminal amino acid that corresponds to the cleavage of plasminogen at or near amino acid position 451.

Although the present angiogenesis inhibitors preferably include a specific C-terminus left by the K-4 protease, the N-terminus thereon can vary depending on several parameters such as the specific inhibitor desired and intended use. Generally, at least one suitable protease, preferably different from the K-4 protease, is used to make the N-terminus. Suitable proteases for making the N-terminus include those that cleave the plasminogen or plasminogen-related molecule once or more than once and in some instances multiple proteases may be used to make a desired N-terminus. Particular angiogenesis inhibitors of this invention will have an N-terminal amino acid between about amino acid 1 and amino acid 400 (inclusive) of plasminogen. More particular angiogenesis inhibitors will have an N-terminus at or near the N-terminal border of the K1 fragment, more particularly, between about amino acid positions 50 and 80 (inclusive) of plasminogen. For some applications, a suitable protease or multiple proteases can be used to provide an N-terminus between about amino acid position 80 and 400 (inclusive) of plasminogen.

As will be appreciated from the foregoing, the N-terminus of a desired angiogenesis inhibitor will be impacted by the protease(s) selected to provide the N-terminus. As an illustration of the invention, the K-4 protease may be used to cleave plasminogen or a plasminogen-related fragment followed by cleavage with a suitable protease or proteases to generate the N-terminus. Alternatively, at least one suitable protease may be used to cleave the plasminogen or related molecule followed by treatment with the K-4 protease. The order in which the K-4 protease and the other protease(s) are used is typically not important so long as the desired angiogenesis inhibitor is obtained. More specific methods for preparing angiogenesis inhibitors are described below.

Accordingly, in one aspect, the present invention features an isolated angiogenesis inhibitor having a molecular weight of between about 40 kDa to 50 kDa as determined by reducing gel electrophoresis and having an amino acid sequence substantially similar to that of the amino acid sequence shown in FIG. 9 or 10 (SEQ ID NO. 2 or 3). Particular angiogenesis inhibitors of this invention will include one or more carbohydrate groups such as glycosyl groups linked to specific amino acids therein. Angiogenesis inhibitors that include at least one glycosyl group are sometimes referred to "glycoforms" to denote potential for differential migration under specific reducing gel electrophoresis. See the examples and discussion below.

The angiogenesis inhibitors of the present invention preferably exhibit significant anti-angiogenic activity in a recognized in vivo or in vitro model for measuring angiogenesis. Several suitable assays to detect and measure angiogenesis are known in the field. Specific assays for testing the angiogenesis inhibitors are described below.

Particular angiogenesis inhibitors of the invention exhibit good activity in an in vitro angiogenesis assay. For example, certain endothelial cell proliferation assays are usually preferred for testing the activity of the angiogenesis inhibitors. More particular angiogenesis inhibitors exhibit a half maximal inhibitory dose ($ID_{50}$) of between about 10 nM and about 500 nM or less in specific endothelial cell proliferation assays described below.

Additional particular inhibitors are capable of inhibiting tumor growth in a recognized in vivo assay for measuring angiogenesis. For example, certain in vivo carcinoma assays such as a lung carcinoma assays are generally preferred although in some instances other in vivo assays may be used. Preferred angiogenesis inhibitors of this invention exhibit significant capacity to inhibit neovascularization and are useful for treating a disease associated with undesired angiogenesis such as cancer. A variety of cancers can be treated in accord with the invention, e.g., prostate cancer, breast cancer, colon cancer, and lung cancer.

Further provided by the invention are pharmaceutical compositions that include at lease one angiogenesis inhibitor having a molecular weight of between about 40 kDa to 50 kDa as determined by reducing gel electrophoresis, and having an amino acid sequence substantially similar to that of the amino acid sequence shown in FIGS. 9 or 10 (SEQ ID NO. 2 or 3). Preferred are sterile pharmaceutical compositions such as those described in more detail below that are well-suited for administration to animals and particularly primates such as humans.

Additionally provided by the present invention is a substantially pure preparation of an angiogenesis inhibitor having: 1) a molecular weight of between about 40 kDa to 50 kDa, and 2) a C-terminal proline residue preferably corresponding to the $Pro^{451}$ residue of plasminogen. Preferred preparations are provided as pharmaceutical compositions and are generally sterile.

In another aspect, the invention features an isolated plasminogen fragment having a molecular weight of between about 50 kDa and 70 KDa and having an amino acid sequence substantially similar to that of the amino acid sequence shown in FIG. 8 (SEQ ID NO: 1). Particular plasminogen fragments include one or more carbohydrate groups such as glycosyl groups bound to specific amino acids therein and may be referred to as "glycoforms". As will be discussed below, the plasminogen fragments have a variety of useful applications including use in the production of certain angiogenesis inhibitors of this invention and use as molecular weight markers for electrophoretic applications.

The invention also provides for a substantially pure preparation of an isolated plasminogen fragment having: 1)

a molecular weight of between about 50 kDa to 70 kD, and 2) a C-terminal proline preferably corresponding to the Pro$^{451}$ residue of plasminogen. Preferred preparations are provided as pharmaceutical compositions and are generally sterile.

As discussed, the present invention features methods for making a variety of angiogenesis inhibitors.

For example, in one aspect, there is provided a method for making an isolated angiogenesis inhibitor having a molecular weight of between about 40 kDa to 50 kDa as determined by reducing gel electrophoresis and having an amino acid sequence substantially similar to that of the amino acid sequence shown in FIG. 9 or 10 (SEQ ID NO. 2 or 3). In one embodiment, the method includes at least one and preferably all of the following steps:

a) contacting plasminogen with an amount of the K-4 venom protease sufficient to cleave the plasminogen into fragments comprising fragments having a molecular weight of between about 50 kDa to 70 kDa as determined by reducing gel electrophoresis, b) contacting the fragments with an amount of at least one other (second) protease sufficient to cleave the fragments at between about amino acid positions 50 and 80 of the plasminogen; and c) isolating the angiogenesis inhibitor from the plasminogen fragments.

The plasminogen used in the method will generally include at least one carbohydrate group and particularly a glycosyl group. In another embodiment, the method can be used with a plasminogen-related molecule instead of plasminogen.

It will be appreciated that fragments made by practice of the method having a molecular weight of between about 50 kDa to 70 kDa will have a C-terminal residue corresponding to amino acid position 451 of plasminogen. In most instances, that C-terminal residue will be proline, e.g., as when human or mouse plasminogen is used in the method.

As noted, the method includes use of at least one (second) protease to cleave the plasminogen fragments having a molecular weight of between about 50 kDa to 70 kDa. Choice of the second protease will be guided by the N-terminus desired. Suitable proteases preferably cleave the plasminogen fragments between about amino acid 50 and amino acid 80 (inclusive) of plasminogen. More particular proteases will be capable of generating an N-terminus at or near the N-terminal border of the first plasminogen kringle. The protease may specifically cleave the plasminogen fragments generated in the method at one or more than one site as needed.

Illustrative of proteases suitable for use in the method are certain proteases and that are capable of cleaving plasminogen between about amino acid positions 1 and 400 (inclusive) with between about amino acids 50 and 80 being generally preferred. Methods for testing whether a particular protease can cleave plasminogen at the specified amino acids are known and include treating plasminogen with the desired protease and separating any fragments produced thereby by reducing gel electrophoresis. Essentially any cleavage site can be readily determined by inspection following use of a suitable fragment visualization technique such as staining.

In an embodiment of the above-described method, the plasminogen fragments having a molecular weight of between about 50 kDa and 70 kDa are purified prior to digestion with the second protease. In a more specific embodiment, the method further includes between steps a) and b), applying the cleaved plasminogen fragments to a first chromatographic implementation and then eluting same from the first chromatographic implementation to obtained a purified fraction thereof.

In a more specific embodiment, the method further includes applying the eluted fragments to a second chromatographic implementation capable that is preferably capable of specifically binding the fragments having the molecular weight of between about 50 kDa to 70 kDa. The fragments are then eluted from the second chromatographic implementation to obtain a substantially pure fraction that includes the fragments.

In another aspect, the invention provides a method for making an isolated angiogenesis inhibitor having a molecular weight of between about 40 kDa to 50 kDa and having an amino acid sequence substantially similar to that of the amino acid sequence shown in FIG. 9 or 10 (SEQ ID NO. 2 or 3). In this embodiment, the method uses specific plasminogen fragments obtained by prior treatment of plasminogen with the K-4 protease. In one embodiment, the method includes at least one and preferably all of the following steps:

a) contacting plasminogen fragments treated with the K-4 protease and having a molecular weight of between about 50 kDa to 70 kD as determined by reducing gel electrophoresis and an amino acid sequence substantially similar to that of the amino acid sequence shown in FIG. 8 (SEQ ID NO: 1) with at least one protease sufficient to cleave the plasminogen fragments between about amino acids 50 and 80 of plasminogen; and b) isolating the angiogenesis inhibitor from the cleaved plasminogen fragments.

The plasminogen fragments will usually include at least one carbohydrate group and particularly a glycosyl group. Suitable proteases that can be used in accord with the method include those discussed above.

In an embodiment of the method, the plasminogen fragments having a molecular weight of between about 50 kDa and 70 kDa can be purified prior to digestion with the protease. In a more specific embodiment, the method further includes between steps a) and b), applying the cleaved plasminogen fragments to a first chromatographic implementation and eluting same from the first chromatographic implementation.

In a more specific embodiment, the method further includes applying the eluted fragments to a second chromatographic implementation capable of specifically binding the fragments having the molecular weight of between about 50 kDa to 70 kDa. The fragments are then eluted from the second chromatographic implementation to obtain a substantially pure fraction of the fragments.

In another aspect of the invention, there is provided a method for making an isolated angiogenesis inhibitor having a molecular weight of between about 40 kDa to 50 kDa as determined by reducing gel electrophoresis and having an amino acid sequence substantially similar to that of the amino acid sequence shown in FIG. 9 or 10 (SEQ ID NO. 2 or 3). In one embodiment, the method includes at least one and preferably all of the following steps:

a) contacting plasminogen with a first protease sufficient to produce plasminogen fragments having a cleavage site between about amino acids 50 and 80 of the plasminogen, b) contacting the plasminogen fragments with an amount of the K-4 protease sufficient to cleave the plasminogen fragments into fragments having a molecular weight of between about 50 kDa to 70 kD; and c) isolating the angiogenesis inhibitor from the cleaved plasminogen fragments.

In one embodiment of the method, the plasminogen includes at least one carbohydrate group and particularly a glycosyl group. Suitable first proteases that can be used with the method are described above.

In an other embodiment of the method, the plasminogen fragments having a molecular weight of between about 50 kDa and 70 kDa can be purified prior to isolating the angiogenesis inhibitor. In a more specific embodiment, the method further includes between steps b) and c) applying the cleaved plasminogen fragments to a first chromatographic implementation and then eluting same from the first chromatographic implementation.

In a more specific embodiment, the method further includes applying the eluted fragments to a second chromatographic implementation capable of specifically binding the fragments having the molecular weight of between about 50 kDa to 70 kDa. The fragments are then eluted from the second chromatographic implementation to obtain a substantially pure fraction of the fragments.

In another aspect, the invention features a method for making an isolated plasminogen fragment having a molecular weight of between about 50 kDa to 70 kDa as determined by reducing gel electrophoresis and having an amino acid sequence substantially similar to that of the amino acid sequence shown in FIG. 8 (SEQ ID NO: 1). As noted, the plasminogen fragments are useful for making the angiogenesis inhibitors of this invention. In one embodiment, the method includes at least one and preferably all of the following steps.

a) contacting plasminogen with an amount of the K-4 protease sufficient to cleave the plasminogen into fragments comprising fragments having a molecular weight of between about 50 kDa to 70 kDa, b) eluting the cleaved plasminogen fragments from a first chromatographic implementation; and c) isolating the fragments having the molecular weight of between about 50 kDa and 70 kDa to make the plasminogen fragment.

In one embodiment of the method, the plasminogen fragment includes at least one carbohydrate group and particularly a glycosyl group.

In a specific embodiment, the method further includes between steps b) and c) applying the eluted fragments to a second chromatographic implementation capable of specifically binding the fragments having the molecular weight of between about 50 kDa to 70 kDa. The fragments are subsequently eluted from the second chromatographic implementation to obtain a substantially pure fraction of the fragments.

A variety of chromatographic implementations can be used to practice the methods, e.g., chromatographic columns such as "spin" columns, and devices employing high performance liquid chromatographic (HPLC) implementations. Nearly any chromatographic implementation can be employed so long as it is capable of isolating the fragments as desired. More specific examples of suitable chromatographic techniques are provided below.

In preferred embodiments of the present methods, the angiogenesis inhibitors are derived from mammalian plasminogen and particularly primate or murine plasminogen with human plasminogen being preferred for many applications.

The K-4 protease used in the present methods can be obtained by one or a combination of strategies. For example, in one approach, the protease is isolated from a fluid obtained from the spitting cobra and is usually purified therefrom to enhance specific activity. In a more specific approach, the protease is isolated from the venom of the cobra by conventional enzyme isolation techniques such as chromatography, filtration or the like. Preferred are isolation techniques that enhance activity of a venom fraction that is capable of specifically cleaving human plasminogen between amino acid positions $Pro^{451}$ and $Asn^{452}$ or $Asp^{432}$ depending on sequence. As noted, the specific cleavage can be determined by a variety of assays including reducing gel electrophoresis.

A particularly preferred K-4 protease for use in accord with the invention is isolated from venom of the cobra and has a molecular weight of between about 5 kDa and 20 kDa and more typically about 10 kDa as determined by reducing gel electrophoresis. Especially preferred methods of isolating the *Naja Nigricollis* protease are described below.

Further provided by the present invention are methods for inhibiting tumor growth in a mammal such as a primate, rodent or domesticated animal. In one embodiment, the method includes administering a therapeutically effective amount of at least one angiogenesis inhibitor sufficient to inhibit the tumor growth. In a specific embodiment, the angiogenesis inhibitor has a molecular weight of between about 40 kDa to 50 kDa as determined by reducing gel electrophoresis and has an amino acid sequence substantially similar to that of the amino acid sequence shown in SEQ ID NOS: 1 or 4. The angiogenesis inhibitor may be administered alone or in combination with other therapeutic agents, e.g., anti-angiogenic compounds or other anti-tumor agents such as chemotherapeutic drugs. Preferably, the angiogenesis inhibitor is administered as a part of a pharmaceutical composition and is sterile.

In a specific embodiment of the method, the mammal is a human and particularly a patient suffering from or suspected of suffering from tumor growth. In a more specific embodiment, the angiogenesis inhibitor is derived from human plasminogen.

Further aspects of the present invention are discussed infra.

BRIEF DESCRIPTION OF THE DRAWINGS

FIGS. 5A and 5B are graphs showing effects of kringles 1–3 and kringle 4 peptides on glu-plasminogen-bone osteonectin interaction measured by TIRFS.

FIG. 8 is a drawing showing a human plasminogen fragment resulting from cleavage with the K4 protease (SEQ ID NO. 1).

FIG. 9 is a drawing showing an angiogenesis inhibitor of the invention resulting from cleavage with plasmin and the K4 protease (SEQ ID NO. 2).

FIG. 10 is a drawing showing an angiogenesis inhibitor of the invention resulting from cleavage with plasmin and the K4 protease (SEQ ID NO. 3).

DETAILED DESCRIPTION OF THE INVENTION

Figure 1:
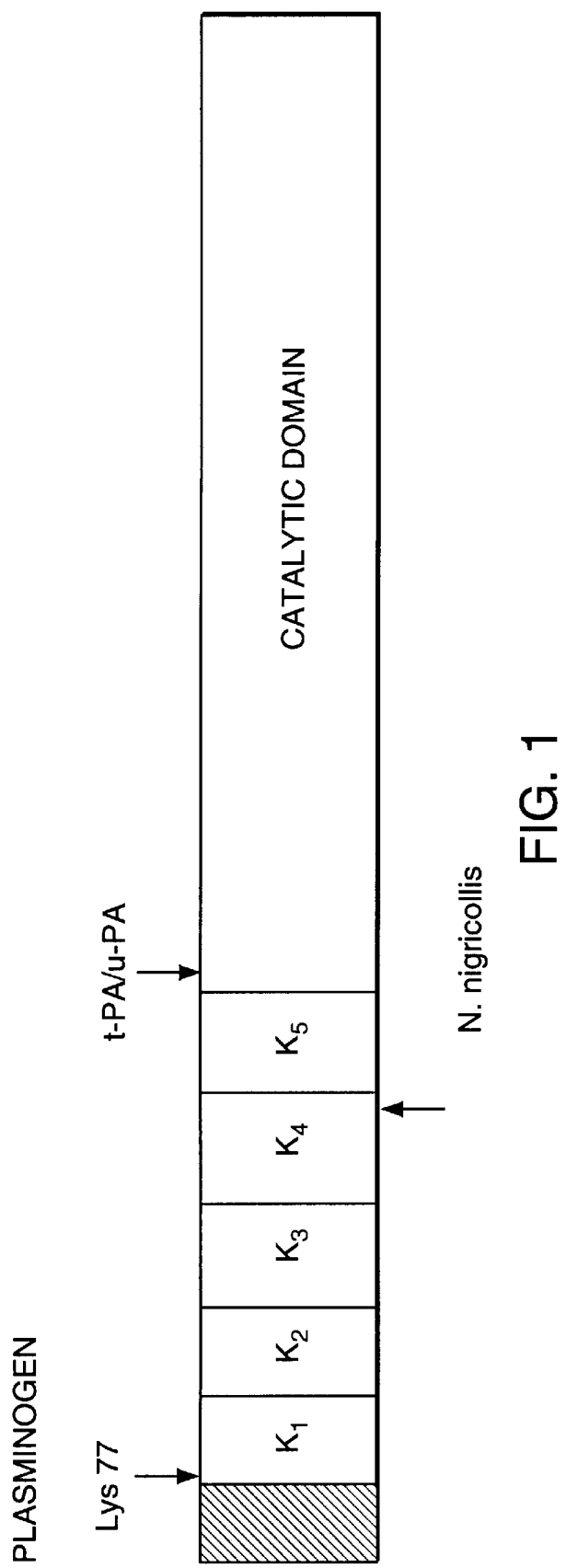
FIG. 1 is a schematic representation of human plasminogen showing the plasminogen kringles (K1–5) linked to the plasmin catalytic domain is referred to as the B chain). Also shown is the plasmin ($Lys^{77}$), u-PA/t-PA and *Naja Nigricollis* ($Pro^{451}$) protease cleavage sites. The *Naja Nigricollis* protease is referred to herein as the K-4 protease.

As discussed above, the present invention features angiogenesis inhibitors and methods of making same from plasminogen or a plasminogen-related molecule. The present invention has a variety of applications including use in treatments to inhibit or block angiogenesis in diseases such as cancer. Treatment methods of the invention generally include administering a therapeutically effective amount of a desired angiogenesis inhibitor to a mammnal such as a human patient in need of such treatment.

Also contemplated is use of the present angiogenesis inhibitors in mouse or primate models for measuring angiogeneis particularly as it relates to cancer or other angiogenesis-related diseases As noted, it has been found that the venom of the spitting cobra *Naja Nigricollis* includes a highly useful protease. That protease (K-4) has been found to be capable of specifically cleaving plasminogen between amino acid positions 451 and 452. The ability to cleave plasminogen once at that site is very advantageous. For example, it provides for production of angiogenesis inhibitors that include, in a single fragment, the first four plasminogen kringles (K1–4). The K1–4 kringles have been shown to be potent anti-angiogenic compounds. Additionally, the proteolytic activity afforded by the K-4 protease provides for especially effective removal of the fifth plasminogen kringle (K5) from the K1–4 fragment. Accordingly, yields and activity of the present angiogenesis inhibitors are positively impacted. See FIG. 1.

Unless specified otherwise, reference herein to an amino acid number or position in an angiogenesis inhibitor means that the amino acid number or position corresponds to the same amino acid number or position in plasminogen. That is, the amino acid number or position used with plasminogen is also used with the angiogenesis inhibitor. As a specific illustration, amino acid 451 or amino acid position 451 of human plasminogen means the $Pro^{451}$ residue of human plasminogen. That $Pro^{451}$ residue is cleaved by the K-4 protease to form the C-terminal end of preferred angiogenesis inhibitors shown in FIGS. 9 and 10 (SEQ ID NO. 2 and 3). In the interest of clarity, the amino acid position or number for plasminogen will be used to describe the angiogenesis inhibitor prepared therefrom herein unless stated otherwise. It will be appreciated that the amino acid sequence of various mammalian plasminogens are highly related, e.g., mouse and human plasminogen. Thus, a specific amino acid number or position in human plasminogen may also be found in other mammalian plasminogens, e.g., murine plasminogen, at that same or closely related amino acid number or position.

DNA and protein sequence information for a variety of mammalian plasminogens have been reported. For example, a mouse plasminogen sequence has been disclosed in U.S. Pat. No. 5,639,725. Other mammalian plasminogen sequences are available from the National Center for Biotechnology Information (NCBI)- Genetic Sequence Data Bank (Genbank). For example, sequence information relating to human plasminogen (Accession No. M74220) can be obtained from Genbank at the National Library of Medicine, 38A, 8N05, Rockville Pike, Bethesda, Md. 20894. Genbank is also available on the internet. See Benson, D. A. et al. (1997) *Nucl. Acids. Res*. 25: 1 for a description of Genbank.

A variety of mammalian plasminogens such as human, bovine, rabbit, horse, porcine, and sheep plasminogen can be obtained from several commercial sources (e.g., Sigma Chemical Co., St. Louis, Mo.). Alternatively, a desired mammalian plasminogen can be isolated from serum or other suitable body fluid using established methods. Preferred sources of plasminogen are described below.

A desired plasminogen including a mammalian plasminogen can be readily tested for capacity to be cleaved by the K-4 protease by standard methods. Illustrative of such methods include conventional protein cleavage assays using reducing gel electrophoresis to identify specific plasminogen fragments and particularly cleavage between amino acid residues corresponding to $Pro^{451}$ and $Asn^{452}$ of human plasminogen. Also contemplated are chromatographic methods designed to facilitate detection of specific peptide fragments including column chromatography, liquid chromatography and especially high performance liquid chromatography (HPLC), diffusion and filtration techniques as well as certain dialysis methods.

As used herein, the term "plasminogen-related molecule" or similar term means an amino acid sequence which can be converted into an enzyme that has plasmin or plasmin-like activity. Illustrative of a plasminogen-related molecule is a molecule having an N-terminus between about amino acid positions 1 to 400 of plasminogen and including linked thereto the plasminogen B chain (plasmin domain).

As noted, the present invention features isolated angiogenesis inhibitors having a molecular weight of between about 40 kDa and 50 kDa as determined by reducing gel electrophoresis and having an amino acid sequence substantially similar to that of the amino acid sequence shown in SEQ ID NOS 1 or 4.

By the term "isolated" is meant that the angiogenesis inhibitor or derivative thereof is at least about 70% (w/w), preferably at least about 85% (w/w), more preferably at least about 90% (w/w) and still more preferably at least about 95% (w/w) of the total protein in a given sample. That is, the isolated angiogenesis inhibitor has been substantially separated from other components that may accompany it such as other proteins and including other plasminogen fragments.

The term "substantially similar" is used herein to denote sequence relationship between two specific sequences. As the term is particularly used to describe sequence relationship between an angiogenesis inhibitor and the amino acid sequence shown in SEQ ID NOS 1 or 4 or SEQ ID NO:2, the term will be understood to refer to amino acid sequence similarity between two molecules. When an amino acid position in both molecules is occupied by the same amino acid, sometimes referred to as a "residue", then the two molecules are homologous (or identical) at that position. Substantial similarity between the two amino acid sequences is a direct function of the number of matching or identical positions, e.g., if 50% of the amino acid positions in the two sequences are homologous then the two sequences are 50% homologous. By "substantially similar" is meant largely but not wholly homologous. More particularly, the term is meant to denote at least about 85%, preferably at least about 90%, more preferably at least about 95% to 98% up to about 100% sequence identity with respect to the amino acid sequences shown in FIG. 9 or 10 (SEQ ID NO: 2 or 3).

Two substantially similar amino acid sequences can be identified by one or a combination of different strategies. For example, in one approach, an angiogenesis inhibitor sequence that is substantially similar to the sequence shown in SEQ ID NOS 1 or 4, can be identified using any one of several available computer programs. Preferred are computer programs that can readily determine identity between two amino acid sequences of known sequence. Exemplary of such programs include BLAST or other suitable program available from the National Library of Medicine (Genbank).

As a more specific illustration, substantial similarity between two amino acid sequences can be determined using the BLAST or other suitable programs such as FASTA. Data can be outputted in a variety of formats to suit intended use. Preferred are formats designed to highlight identical and non-identical amino acids. Any substantial similarity between the molecules can be determined, e.g., by inspection of identical (matching) and non-identical amino acids. See S. Altschul et al. *J. Mol. Biol.*, 215:403–410 (1990); and S. Altschul et al. *Nuc. Acids Res.*, 25: 3389–3402 (1997)for disclosure relating to the BLAST program.

The angiogenesis inhibitors of the present invention thus include the specific amino acid sequence shown in FIGS. 9 and 10 (SEQ ID NOS: 2 and 3), as well as amino acid substitutions or deletions (contiguous or non-contiguous) of those sequences provided the resulting sequence is substantially similar to the sequence shown in SEQ ID NOS. 1, 2, 3 or 4. Further contemplated are amino acid sequences that are substantially similar to those shown in FIG. 9 or 10 (SEQ ID NO: 2 or 3) and include modified amino acid residues, e.g., amino acid residues comprising attached carbohydrate groups and particularly glycosyl groups.

Also contemplated are angiogenesis inhibitors in which one or more amino acids have been added, i.e., to facilitate protein purification or identification. Preferably, between about 1 to 50 amino acids are added and more preferably between about 5 to 25 amino acids are added. The amino acids can be added by several strategies with peptide synthetic methods being generally preferred for many applications.

The isolated angiogenesis inhibitors of the present invention are specific plasminogen fragments that are produced by treating plasminogen or a plasminogen-related molecule with the K-4 protease. The angiogenesis inhibitors will generally include a C-terminal amino acid that corresponds to amino acid position 451 of human plasminogen. Nearly any mammalian plasminogen is suitable for making the angiogenesis inhibitors so long as the cobra protease can specifically cleave the plasminogen at an amino acid position that corresponds to amino acid position 451 of plasminogen. In a specific embodiment, the angiogenesis inhibitors will be derived from human plasminogen and the C-terminal amino acid of the angiogenesis inhibitor will be a proline residue corresponding to $Pro^{451}$ of human plasminogen. In another embodiment, the angiogenesis inhibitors will be derived from mouse plasminogen and the C-terminal amino acid of the inhibitor will also be a proline residue corresponding to $Pro^{451}$ of mouse plasminogen.

As noted above, the amino acid sequence of particular angiogenesis inhibitors may vary slightly between mammalian species. For example, the amino acid sequence of the angiogenesis inhibitor shown in FIG. 9 or 10 (SEQ ID NO: 2 or 3) will be substantially similar to the sequence of several other mammalian angiogenesis inhibitors. Specific examples of angiogenesis inhibitors include those obtained from primate, e.g., human or monkey; bovine, equine, sheep, murine or porcine plasminogen with human plasminogen being preferred for many applications.

In contrast to the specific C-terminal amino acid of the present go-I. angiogenesis inhibitors, the N-terminal amino acid will vary. In general, the N-terminal amino acid is formed by contacting a desired plasminogen, or a plasminogen-related molecule with at least one protease or other suitable proteolytic agent capable of cleaving the plasminogen or plasminogen-related molecule. The number of proteases will vary depending on intended use but will typically be between about 1 and 3 with one protease being generally preferred. Preferred are certain serine proteases and metalloproteases that are capable of cleaving plasminogen between about amino acid positions 1 and 400 (inclusive). More preferred are serine proteases and metalloproteases that are capable of cleaving plasminogen at least one site between about amino acids 50 and 80 (inclusive) of plasminogen. Preferred in some instances are proteases that can cleave plasminogen between about amino acids 80 and 400 (inclusive) of plasminogen. The proteases may cleave the plasminogen or plasminogen-related molecule between about 1 and 5 times, preferably between about 1 and 3 times with one cleavage site being preferred. Illustrative of such proteases include elastase, matrilysin (MMP-7), stromlysin and gelatinase B/Type IV collegenase (MMP-9).

An especially preferred protease is plasmin. Specific methods for making and using plasmin and other specified proteases have been described. See e.g., U.S. Pat. No. 5,639,725; Lijnen, H. R. et al. (1998) *Biochem.* 37: 4699; Stathakis, P. et al. (1997) *J. Biol. Chem.* 272: 20641; Patterson, B. C. and Sang, Q. A. (1997) *J. Biol. Chem.* 272: 28823; O'Reilly, M. S. et al. (1994), supra.

See FIG. 1 showing human plasminogen comprising a plasmin cleavage site at amino acid position 77 and the *Naja nigricollis* (K-4) protease cleavage site at position 451. The resulting fragment is the preferred angiogenesis inhibitors shown in FIGS. 9 and 10 (SEQ ID NOS: 2 and 3).

Additionally preferred angiogenesis inhibitors of this invention will usually include between about 50 and 500 amino acids, preferably between about 100 and 451 amino acids, more preferably between about 250 and 451 amino acids, and even preferably between about 350 and 451 amino acids. More preferred are angiogenesis inhibitors that include between about 370 and 451 amino acids. The angiogenesis inhibitors or derivatives thereof can be bound useful moieties if desired which permit ready identification such as a radionuclide, fluorescent or chemical identifier. The number of amino acids can be readily determined by a variety of techniques including convenient peptide sequencing and reducing gel electrophoresis.

Preferred angiogenesis inhibitors of the invention demonstrate substantial anti-angiogenic activity in one or more recognized assays for measuring angiogenesis. Suitable assays include those that are capable of monitoring and preferably quantitating the proliferation of specific cells such as endothelial cells and tumor cells. Particular examples of such assays include certain endothelial cell proliferation assays, murine corneal angiogenesis assays, and a Lewis lung carcinoma metastasis assay. See e.g., U.S. Pat. No. 5,639,725 and references cited therein for disclosure relating to the assays.

Endothelial cell proliferation is a significant component of angiogenesis. A preferred assay for quantitating anti-angiogenic activity is an endothelial cell proliferation assay. Preferred are certain assays that monitor proliferation of capillary cells in response to growth factors and can detect and preferably quantitate inhibition of fetal growth factor (FGF) induced proliferation of capillary endothelial cells. A more specific assay is a bovine capillary endothelial cell assay that can detect and quantitate inhibition of bFGF induce proliferation of bovine endothelia. A particular assay is conducted, e.g., by:

a) maintaining bovine capillary endothelial cells (BCEs) in suitable medium including 1) bFGF, e.g., commercially available recombinant bFGF, e.g., at a concentration of about 1 to 5 ng/ml with DMEM media being generally preferred for most assays, b) suspending the cells and counting same with a suitable cell counting device, e.g., a hemocytometer, and adjusting the cell suspension to about 25,000 cells/ml, c) plating the cells onto a suitable multi-well cell culture plate, e.g., a 24-well microplate, in DMEM media including: 1) the bFGF and 2) and between about 10 and 500 nM of an angiogenesis inhibitor, e.g., the amino acid sequence of FIG. 9 or 10 (SEQ ID NO: 2 or 3); and d) incubating the cells for about 24 to 72 hours in the media and counting same to detect, and quantitate if desired, any decrease in proliferation of the cells.

The above-described assay will usually be conducted by including a suitable control culture. A preferred control culture is prepared by performing steps a) to d) above, except that the angiogenesis inhibitor is usually not added. However, if desired, administration of the angiogenesis inhibitor can be substituted with saline. It will be appreciated that once proliferation in the control culture is established, preparation of a control culture need not be repeated for every assay.

Data obtained from the assay can be presented in a number of formats although a graphical representation showing the percent change in cell number (compared to the control culture) versus the concentration of angiogenesis inhibitor is generally useful for most applications. More specific methods for conducting the bovine capillary endothelial cell assay have been disclosed. See e.g., O'Reilly, M. S. et al. (1994), supra; Cao, Y. et al. (1996), supra; and U.S. Pat. No. 5,639,725.

References herein to an "endothelial cell proliferation assay" or related term or phrase refers to the preferred assay described above and includes the above steps a) to d). Suitable protocols for preparing and using BCEs have been described. See e.g., U.S. Pat. No. 5,639,725 and Folkman, J. et al. (1979) *PNAS(USA)* 76: 521. If desired, the BCEs may be substituted with other suitable cells including bovine aortic endothelial cells and EOMA (murine hemangioendothelioma cells) in accord with known techniques.

More preferred angiogenesis inhibitors of this invention will exhibit substantial anti-angiogenic activity in the endothelial cell proliferation assay. Especially preferred inhibitors will exhibit and $ID_{50}$ of between about 10 nM and 500 nM or less in the assay, preferably between about 50 nM and 200 nM, and more preferably between about 100 nM and 150 nM.

If desired, angiogenesis inhibitors of this invention may be further tested in recognized in vivo models that measure anti-angiogenesis activity. For example, additionally preferred angiogenesis inhibitors of this invention will exhibit significant anti-angiogenic activity in the Lewis lung carcinoma metastasis assay. Preferably, the inhibitors are capable or decreasing presence of visible lung metastases in the assay by between about 2 and 20 fold or more, more preferably between about 5 and 10 fold when compared to a suitable control. Additionally, the inhibitors will be capable of reducing lung weight by between about 2 and 10 fold, preferably between about 2 and 5 fold compared to the control. A preferred Lewis lung carcinoma metastasis assay is performed by:

a) administering to a mouse (C57BL6/J strain, Jackson Labs Bar Harbor Me), about $1\times10^6$ cells of a highly metastatic Lewis Lung carcinoma cell line (LLC-Low), b) incubating the LLC-Low cells in the mouse for a time sufficient to establish tumors, e.g., for about 10 to 20 days, preferably about 15 days, c) administering, preferably at least daily, between about 1 $\mu$g/g mouse and 50 $\mu$g/g mouse of a desired angiogenesis inhibitor, preferably between about 2 $\mu$g/g mouse and 10 $\mu$g/g mouse of the inhibitor, e.g., the amino acid sequence shown in FIG. 9 or 10 (SEQ ID NO: 2 or 3); and d) detecting a decrease in tumor metastases to the lung of the mouse when compared to a suitable control.

The Lewis lung carcinoma metastases assay described above may be conducted by including a suitable control animal. A preferred control animal is prepared by conducting steps a) to c), above, except that the angiogenesis inhibitor is not added. Preferably a sham procedure is performed in which administration of the angiogenesis inhibitor is substituted with, e.g., a saline injection. It will be appreciated once metastases of Lewis lung cells in the mouse is established the preparation of control animals need not be performed for every assay.

Data obtained from the Lewis Lung carcinoma metastases assay can be presented in a number of formats although a graphical representation showing the number of surface lung metastases or lung weight versus a suitable control is generally preferred for most applications. More specific methods for conducting the Lewis Lung carcinoma assay and for isolating the LLC-low cell line have been disclosed See e.g., O'Reilly, M. S. et al. (1994), supra; and U.S. Pat. No. 5,639,725.

Additionally preferred are angiogenesis inhibitors that include nearly all of the first four plasminogen kringles K1–4, preferably at least about 90%, at least about 95% or more of the kringles. The amino acid sequence of the plasminogen kringles has been disclosed. See e.g., Sottrup-Jensen, L. et al. (1978) *Prog. Chem. Fibrinolysis Thrombolysis* 3: 191.

Particularly preferred angiogenesis inhibitors have the amino acid sequence shown in FIGS. 9 and 10 (SEQ ID NO: 2 and 3). The inhibitors can be made by contacting human plasminogen with the K-4 protease and plasmin and then purifying the amino acid sequence from other plasminogen fragments by methods described herein. As noted, the order in which the protease and plasmin contacts the plasminogen or other suitable molecule is not important so long as the desired angiogenesis inhibitor is obtained. In the embodiment shown in SEQ ID NO. 2, the amino acid sequence spans residues 77 to 451 of plasminogen. In the embodiment shown in SEQ ID NO. 3, plasminogen is cleaved with plasmin and the K-4 protease to make an amino acid sequence that spans 78 to 451 of plasminogen.

Further preferred angiogenesis inhibitors of the present invention are glycosylated at an amino acid that corresponds to amino acid $Asn^{288}$ of human plasminogen and preferably includes a sialic acid-galactose-and mannose-containing oligosaccharide (glycoform I). In another specific embodiment, the angiogenesis inhibitor is glycosylated at an amino acid that corresponds to Thr$^{345}$ of human plasminogen and includes an N-acetyl galactosamine-containing oligosaccharide (glycoform II). See e.g., Hayes, M. L. and Castellino F. J. (1979) *J. Biol. Chem.* 254: 8768–8771; 8772–8776, 8777–8780, for additional disclosure relating to glycosylation sites on plasminogen and related molecules.

Also preferred is a plasminogen fragment having the amino acid sequence shown in FIG. 8 (SEQ ID NO: 1). In a more preferred embodiment, the plasminogen fragment is glycosylated at an amino acid that corresponds to amino acid Asn$^{288}$ of plasminogen and preferably includes a sialic acid-galactose-and mannose-containing oligosaccharide (glycoform I). In another specific embodiment, the plasminogen fragment is glycosylated at an amino acid that corresponds to Thr$^{345}$ of plasminogen and includes an N-acetyl galactosamine-containing oligosaccharide (glycoform II). As noted, the plasminogen fragment is useful, e.g., for preparing certain angiogenesis inhibitors of this invention.

The plasminogen fragment shown in FIG. 8 (SEQ ID NO. 1) includes what is sometimes referred to as a terminal activation peptide or like term. The terminal activation peptide corresponds to about amino acids 1 to about 77 of plasminogen. Removal of the terminal activiation peptide has been reported to impact anti-angiogenic activity. See e.g., Stathakis, P. et al. (1997) *J. Biol. Chem.* 272:20641.

It is preferred that the angiogenesis inhibitors of the present invention be substantially pure. That is, the inhibitors have been isolated and are present in at least 90 to 95% homogeneity (w/w). Angiogenesis inhibitors having at least 98 to 99% homogeneity (w/w) are most preferred for many pharmaceutical, clinical and research applications. Once substantially purified the inhibitors should be substantially free of contaminants for therapeutic applications. Once purified partially or to substantial purity, the angiogenesis inhibitors can be used therapeutically, or in performing in vitro or in vivo assays as disclosed herein. Substantial purity can be determined by a variety of standard techniques such as chromatography and gel electrophoresis.

Preferred methods of the invention include treating a desired mammalian plasminogen such as human or mouse plasminogen with the K-4 protease to provide the C-terminus. The N-terminus of the inhibitor is made by further treatment with at least one and preferably one suitable protease. The angiogenesis inhibitor can be separated from undesired proteins such as other plasminogen fragments by nearly any acceptable means including chromatography, filtration, electrophoresis, etc. In one embodiment, the methods employ a first chromatographic implementation which can be a column that includes lysine-Sepharose. Methods for preparing lysine-Sepharose columns are known. Fragments are purified on the column and then eluted. In a more specific embodiment, the methods include purifying the eluted fragments on a second chromatographic implementation which can include a anti-plasminogen antibody or antigen binding fragment thereof. In a more specific embodiment, the anti-plasminogen antibody is capable of specifically binding the kringle 5-B chain region of human plasminogen.

As noted, the angiogenesis inhibitors of the present invention can be separated and purified, e.g., from other plasminogen fragments, by appropriate combination of known techniques. These methods include, for example, methods utilizing solubility such as salt precipitation and solvent precipitation, methods utilizing the difference in molecular weight such as dialysis, ultra-filtration, gel-filtration, and SDS-polyacrylamide gel electrophoresis, methods utilizing a difference in electrical charge such as ion-exchange column chromatography, methods utilizing specific affinity such as affinity chromatograph, methods utilizing a difference in hydrophobicity such as reverse-phase high performance liquid chromatograph and methods utilizing a difference in isoelectric point, such as isoelectric focusing electrophoresis, metal affinity columns such as Ni-NTA. See generally Sambrook et al. and Ausubel et al. supra for disclosure relating to these methods.

Particularly preferred are methods of the invention involve production of plasminogen fragments and particularly angiogenesis inhibitors by treating human plasminogen or related molecule with the K-4 protease and plasmin. As noted, the order in which the proteases are used is not important so long as desired products are obtained.

As discussed, the present invention includes anti-angiogenic compositions and methods for the treatment of diseases and processes that are mediated by or associated with angiogenesis. An illustrative composition is the angiogenesis inhibitor shown in FIG. 9 or 10 (SEQ ID NO: 2 or 3). This inhibitor is preferably made by methods described herein. Alternatively, the inhibitor can be synthesized by chemical or biological methods (e.g. cell culture, recombinant gene expression, and in vitro enzymatic catalysis of plasminogen or plasmin to yield the active inhibitor). Recombinant techniques include gene amplification from DNA sources using the polymerase chain reaction (PCR), and gene amplification from RNA sources using reverse transcriptase/PCR. See e.g., *Solid Phase Peptide Synthesis: A Practical Approach* E. Atherton and R. C. Sheppard, IRL Press, Oxford England. Similarly, multiple fragments can be synthesized which are subsequently linked together to form larger fragments.

The present invention further provides kits for making and using the angiogenesis inhibitors of the present invention. In one embodiment, there is provided a kit including a container means including one or more of the inhibitors. Preferred is a kit that includes an angiogenesis inhibitor having substantial similarity to the amino acid sequence shown in FIG. 9 or 10 (SEQ ID NO: 2 or 3). Additionally preferred is the amino acid sequence shown in SEQ ID NOS 1 or 4 in which amino acids corresponding to Asn$^{288}$ and/or Thr$^{345}$ of plasminogen are glycosylated as described above. In another embodiment, a kit of this invention will include directions for making one or more of the angiogenesis inhibitors described herein. Such kits may further include any suitable mammalian plasminogen preferably human or mouse plasminogen, and one or more additional proteases or proteolytic agents for making the inhibitors.

As noted above, the present invention provides methods and compositions for treating diseases and processes mediated by undesired and uncontrolled angiogenesis by administering to a human or animal a composition comprising a substantially purified angiogenesis inhibitor in a dosage sufficient to inhibit angiogenesis. Preferred are those angiogenesis inhibitors which exhibit significant activity in the assays described herein and particularly in the BCE and Lewis lung carcinoma assay. Thus, the present invention is particularly useful for treating or for repressing the growth of tumors. Administration of the inhibitor to a human or animal with prevascularized metastasized tumors will prevent the growth or expansion of those tumors.

More particularly, the methods and compositions can be used to treat diseases and processes that are mediated by angiogenesis including, but not limited to, hemangioma, solid tumors, leukemia, metastasis, telangiectasia psoriasis scleroderma, pyogenic granuloma, Myocardial angiogenesis, plaque neovascularization, coronary collaterals, ischemic limb angiogenesis, corneal diseases, rubeosis, neovascular glaucoma, diabetic retinopathy, retrolental fibroplasia, arthritis, diabetic neovascularization, macular degeneration, wound healing, peptic ulcer, fractures, keloids, vasculogenesis, hematopoiesis, ovulation, menstruation, and placentation.

As used herein, the term "angiogenesis" means the generation of new blood vessels into a tissue or organ. Under normal physiological conditions, humans or animals undergo angiogenesis only in very specific restricted situations. For example, angiogenesis is normally observed in wound healing, fetal and embryonal development and formation of the corpus luteum, endometrium and placenta. The term "endothelium" means a thin layer of flat epithelial cells that lines serous cavities, lymph vessels, and blood vessels. The term "endothelial inhibiting activity" means the capability of a molecule to inhibit angiogenesis in general and, for example, to inhibit the growth of bovine capillary endothelial cells in culture in the presence of fibroblast growth factor.

The angiogenesis inhibitors of the present invention can be used therapeutically as a long-term anti-metastatic therapy. Also, the molecules can be used to develop methods and kits for measuring the concentration of molecules administered therapeutically in a body fluid such as urine or blood. By measuring the concentration of the angiogenesis inhibitor molecules in a body fluid, such as blood or urine, one can diagnose a cancer or determine the prognosis of the disease.

As discussed above, the present angiogeneis inhibitors can be tested for capacity to treat diseases or processes that are mediated by, or involve, angiogenesis. The present invention includes the method of treating an angiogenesis associated disease with an effective amount of at least one inhibitor molecule. The angiogenesis associated diseases include, but are not limited to, solid tumors; blood born tumors such as leukemias; tumor metastasis; benign tumors, for example hemangiomas, acoustic neuromas, neurofibromas, trachomas, and pyogenic granulomas; rheumatoid arthritis; psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; and wound granulation. The angiogenesis inhibitors are useful in the treatment of disease of excessive or abnormal stimulation of endothelial cells. These diseases include, but are not limited to, intestinal adhesions, atherosclerosis, scleroderma, and hypertrophic scars, i.e., keloids. The inhibitors can be used as a birth control agent by preventing vascularization required for embryo implantation.

The angiogenesis inhibitors of this invention may be used as a sole active agent or in combination with other agents such as angiostatin or chemotherapeutic agents. For example, a tumor may be treated conventionally with surgery, radiation or chemotherapy combined with treatment involving administration of one or more of the angiogenesis inhibitors. The inhibitors may be further administered to the patient to extend the dormancy of micrometastases and to stabilize any residual primary tumor.

As discussed above, angiostatin is usually derived from plasma and forms of angiostatin have been described, e.g., by O'Reilly, M. S. (1997), supra. For example, murine angiostatin is defined as the elastase-derived product of murine plasminogen that includes amino acid residues 98 to 440. There are two possible amino-terminii for the human elastase-derived angiostatin molecules: 97 to 441 and 99 to 441. A recombinant murine form of angiostatin has been defined as amino acids 98 to 458 of murine plasminogen. See Wu, Z. et al. (1997) *Biochem. Biophys. Res. Commun.* 236: 651.

The angiogenesis inhibitors of the invention can be provided as isolated and substantially purified protein fragments in pharmaceutically acceptable formulations using formulation methods known to those of ordinary skill in the art. These formulations can be administered by standard routes. In general, the combinations may be administered by the topical, transdermal, intraperitoneal, oral, rectal or parenteral (e.g., intravenous, subcutaneous or intramuscular) mute. In addition, the angiostatin may be incorporated into biodegradable polymers allowing for sustained release of the compound, the polymers being implanted in the vicinity of where drug delivery is desired, for example, at the site of a tumor or implanted so that the inhibitor is slowly released systemically. The biodegradable polymers and their use are described, for example, in detail in Brem et al. (1991), *J. Neurosurg.* 74:441.

The dosage of the angiogenesis inhibitor of the present invention will depend on the disease state or condition being treated and other clinical factors such as weight and condition of the human or animal and the route of administration of the compound. For treating humans or animals, between approximately 0.5 mg/kilogram to 500 mg/kilogram of the inhibitor can be administered. Depending upon the half-life of the inhibitor in the particular animal or human, the inhibitor can be administered between several times per day to once a week. It is to be understood that the present invention has application for both human and veterinary use. The methods of the present invention contemplate single as well as multiple administrations, given either simultaneously or over an extended period of time.

The angiogenesis inhibitor formulations include those suitable for oral, rectal, ophthalmic (including intravitreal or intracameral), nasal, topical (including buccal and sublingual), vaginal or parenteral (including subcutaneous, intraperitoneal, intramuscular, intravenous, intradermal, intratracheal, and epidural) administration. The formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or, multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of the administered ingredient. It should be understood that in addition to the ingredients, particularly mentioned above, the formulations of the present invention may include other agents conventional in the art having regard to the type of formulation in question.

Plasminogen binding to osteonectin is believed to be mediated through the kringle 1, and possibly kringle 4, domains of plasminogen.

The present invention is further illustrated by the following Examples. These examples are illustrative of the present invention and should not be construed as a limitation thereof.

All documents referenced herein are incorporated by reference in their entirety.

REFERENCE EXAMPLE 1

The isolation and purification of the *Naja Nigricollis* K-4) protease generally followed the disclosure of Hassan, M. I (1985) Ph.D. Thesis entitled *Selected Proteolysis of Prothrombin, Factor V, Factor VIII and Factor X with the Venom Proteases of Naja Nigricollis and Cerastes Cerastes* (Ain Shams University, Cairo, Egypt); the disclosure of which is incorporated herein by reference.

The isolation of the active protease was accomplished by chromatography of crude venom over a gel filtration column (Sephadex G-100), followed by rechromatography of the active fractions over a cation exchanger column (Sulfopropyl-Sephadex C50). *Naja Nigricollis* venom can be obtained from a variety of commercial sources, e.g., Sigma Chemical Co. (St. Louis, Mo.).

1. Gel filtration over Sephadex G-100:

One hundred milligrams of crude lyophilized *Naja Nigricollis* venom was dissolved in 2 mls of 0.025 M sodium phosphate, 0.1 M NaCl, pH 6.5 plus 1 ml 50% glycerol water (V/V) and applied to a column (1.6×80 cm), of Sephadex G-100, previously equilibrated with 600 ml of the same buffer at 4° C. Elution was achieved by 0.025 M sodium phosphate, 0.1 M NaCl, pH 6.5. Absorbance of the elute was recorded at 280 nm, and fractions of 2 mls were collected. The active protease-containing fractions were identified by assaying each pool corresponding to each peak for it's ability to cleave the prothrombin molecule over various incubation periods.

The assay was performed by incubating 1 ug volume of each pool with 100 ug volume of human prothrombin after dialysis versus 0.02 M Tris. HCl, 0.15 M NaCl, pH 7.4, in the presence of 29 uM phospholipid vesicles (75% phosphatidyl choline, 25% phosphatidyl serine) and 2.0 mM calcium chloride to the final concentration. The reaction was carried out at 37° C. and the results were analyzed by SDS-polyacrylamide slab gel electrophoresis according to the method of Laemelli.

2. Rechromatography of the active fractions on Sulfopropyl-Sephadex C50:

The activity-containing fractions obtained by sephadex G-100 chromatography were further purified by Sulfopropyl-Sephadex C50 chromatography. Fractions from the sephadex G-100 column containing the active protease were pooled together and dialyzed versus 0.025 M sodium phosphate, pH 6.5 for an overnight with 2 changes of the dialyzing buffer. The dialyzed sample was applied to a Sulfopropyl-Sephadex C50 column (4×1.2 cm), previously equilibrated in the same buffer at 4° C. The column was washed with the equilibrating buffer until the effluent has an absorbance of zero at 280 nm. The eluting buffer was then changed to 0.05 M sodium phosphate, pH 6.5, another peak was eluted and the flow was continued until its absorbance at 280 nm was zero. Further elution was accomplished with 0.1 M sodium phosphate, pH 6.5. The last peak was eluted by 0.25 M sodium phosphate, pH 6.5. The activity-containing fractions were identified by assaying each pool corresponding to each peak obtained by the different ionic strengths. The assay was performed by incubating lug volume of each pool and 100 ug volume of dialyzed human prothrombin versus 0.02 M Tris. HC1, 0.15 M NaCl, pH 7.4. Calcium chloride and phospholipid vesicles were added in a 2.0 mM and 29 uM to the final concentration, respectively. The reaction was carried out at 37° C. and the results were analyzed by SDS-polyacrylamide slab gel electrophoresis according to the method of Laemelli. The active fractions were pooled together, concentrated by the addition of solid ammonium sulfate to 80% saturation. The resulting precipitate was dissolved in a minimal volume of 50% glycerol wter (V/V) and stored at −20 ° C.

REFERENCE EXAMPLE 2

Proteolysis of human plasminogen was performed essentially as described by Omar, M. N. N (1986) Ph.D. Thesis entitled *The Studies of the Utility of the Cerastes Cerastes Pro-Leu Cleaving Enyzme and other Venoms For Sequence Analysis in Protein C* (Ain Shams University, Cairo, Egypt); the disclosure of which is incorporated herein by reference.

1. Effect of urokinase on the *Naja Nigricollis* cleaved plasminogen

Cleavage of human plasminogen with *Naja Nigricollis* venom protease over a period of 60 minutes, followed by the addition of urokinase to the remaining reaction mixture, and further incubation for 60 minutes was carried out as follows:

Two $\mu$g of *Naja Nigricollis* venom protease were incubated at 37° C. with 100 $\mu$g of human plasminogen in the presence of 2 mM $CaCl_2$, 0.02M Tris, HCl, 0.1 5M NaCl, pH 7.4 in a total volume of 200 ul. After a 60 minute incubation, an aliquot of 40 $\mu$l was taken, quenched with glacial acetic acid, and to the remaining reaction mixture, 0.0032 units of urokinase in 0.02M Tris- HCl, 0.15M NaCl, pH 7.4 were added, and the incubation was continued for another 60 minutes. At time intervals, aliquots of 40 $\mu$l were taken, quenched with glacial acetic acid, frozen, lyophilized, and prepared for electrophoresis on a gradient 8–18% SDS-polyacrylamide slab gel Laemmli, U. K. (1970) *Nature* 227: 680.

2. Lysine—substituted—sepharose affinity chromatography of the *Naja Nigricollis* cleaved plasminogen 1 mg of human plasminogen was incubated at 37° C. with 8 $\mu$g of *Naja Nigricollis* protease in 0.02M Tris HCl, 0.15M NaCl, 2 mM $CaCl_2$, pH 7.4, in a total reaction volume of 1 ml.

After a 3 hour incubation, the reaction mixture was applied directly over a column (1×5 cm) packed with lysine-Sepharose (Sigma) equilibrated at room temperature with 0.1M Na phosphate pH 8.0. The column was washed with the same buffer, until the effluent had an absorbance of zero at 280 nm. A linear gradient of e-amino caproic acid (0.000M to 0.025M) in the same buffer was then applied, where the second peak was eluted. Fractions of 1 ml were collected. The material(s) in each peak was pooled and kept at 4° C. for further investigations.

3. The effect on human plasminogen

The progress of the proteolytic reaction was conveniently monitored with the use of SDS electrophoretic analysis of aliquots of 40 $\mu$l taken from the reaction mixture at various time intervals. The results show progressive degradation of the plasminogen molecule by incubation with the venom. A low proportion of intact plasminogen remained after 60 minutes of incubation.

With the degradation of the plasminogen molecule, a lower cleavage product appeared as a sharp band, gradually increasing in density by time, at a position corresponding to a molecular weight of about 38,000 daltons. During incubation with urokinase, plasminogen is proteolytically cleaved to give rise to the serine protease plasmin. Plasmin is a two-chain molecule with two interchain disulfide bonds. When electrophoresed under reduced conditions, plasmin shows a heavy (A) chain with a molecular weight of 48,800 daltons and a light (B) chain with a molecular weight of 25,700 daltons. Although the plasminogen molecule was readily hydrolyzed by the purified Naja Nigricollis venom protease, the degradation products were totally different from urokinase mediated degradation of plasminogen, indicating different points of cleavage.

EXAMPLE 1

Figure 2A:
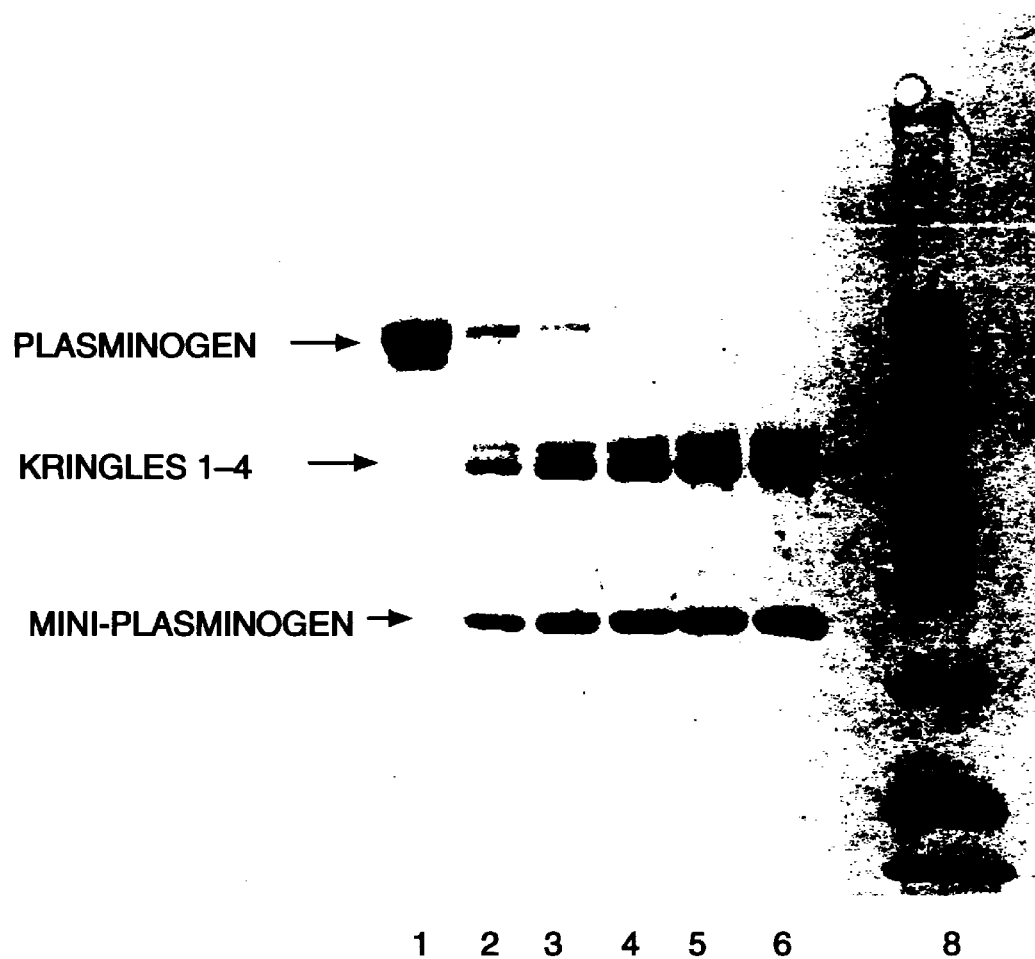
FIGS. 2A and 2B are representations of polyacryamide gels showing plasminogen fragments (2A) produced at various times by treatment with the K-4 protease. (2B) digestion of plasminogen with the K-4 protease.

Characterization of N. nigricollis (K-4) Protease Cleavage of Plasminogen:

Incubation of human plasma derived glu-plasminogen with the N. nigricollis protease yielded three peptide fragments (FIG. 2A, lanes 2–6), two fragments of approximately 45,000 molecular weight and a third peptide fragment with a molecular weight of approximately 35,000 D. Uncleaved plasminogen was evident at a molecular weight of approximately 88,000 D (FIG. 2A, lane 1). Proteolysis of glu-plasminogen to yield the peptide fragments appeared to be complete by 60 minutes when incubated with the N. nigricollis protease at 37° C. (FIG. 2A, lane 4). Incubation of the N. nigricollis enzyme-proteolyzed plasminogen with S2251, a chromogenic substrate for plasmin, showed no evidence of substrate hydrolysis. Although the protease cleaves plasminogen, the zymogen does not appear to be activated.

The two peptide fragments of approximately 45,000 D bound to lysine-Sepharose while the smaller peptide fragment did not. The 35,000 D plasminogen peptide was recognized by αHPg-247, a monoclonal antibody which recognizes an epitope in the kringle 5-B chain region of plasminogen. The binding affinities of the peptides allowed for isolation of the cleavage products.

FIG. 2A is explained in more detail as follows:

The figure shows a time course of N. nigricollis enzyme cleavage of plasminogen at 37° C. Glu plasminogen, at a concentration of 1 mg/ml, was incubated with the enzyme, at a concentration of 8 µg/ml, for 120 minutes at 37° C. Aliquots were removed at indicated time points and analyzed by SDS-PAGE, 10%, under non-reducing conditions. Lane 1: 0 time, plasminogen alone, lane 2: 15 minutes incubation with enzyme, lane 3: 30 minutes, lane 4: 60 minutes, lane 5: 90 minutes and lane 6: 120 minutes incubation. Lane 7 contains molecular weight markers.

Figure 2B:
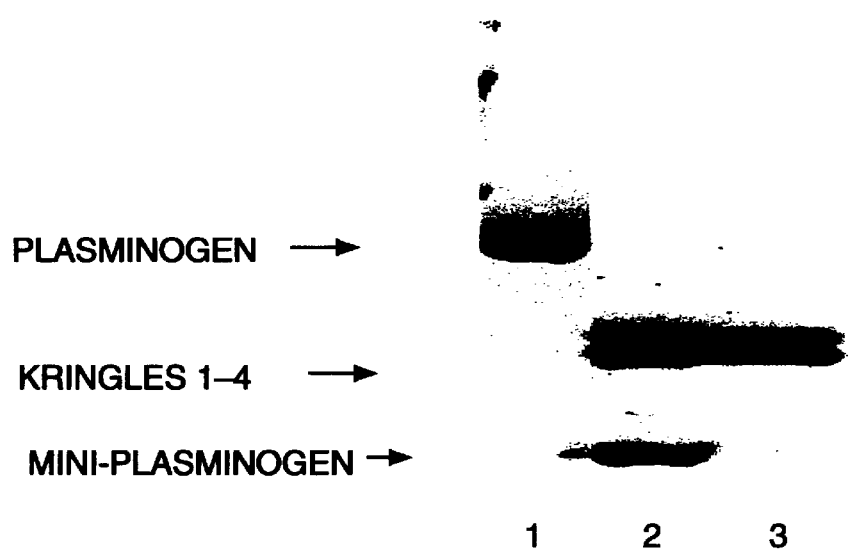

FIG. 2B is explained as follows:

The figure shows the isolated K1–4 fragment obtained by cleavage of glu-plasminogen with the K-4 protease. Lane 1 contains 10 µg of purified glu-plasminogen (pg). Lane 2 contains 10 µg of glu-plasminogen treated with 1 µg K-4 protease for 60 minutes at 37° C. The kringles 1–4 fragment (k1–4) and kringle 5-B chain domain (mini-pg) are present as is intact plasminogen. Lane 3 contains 10 µg of purified kringles 1–4. The analysis was conducted by SDS-PAGE, 10%, under non-reducing conditions.

Figure 3:
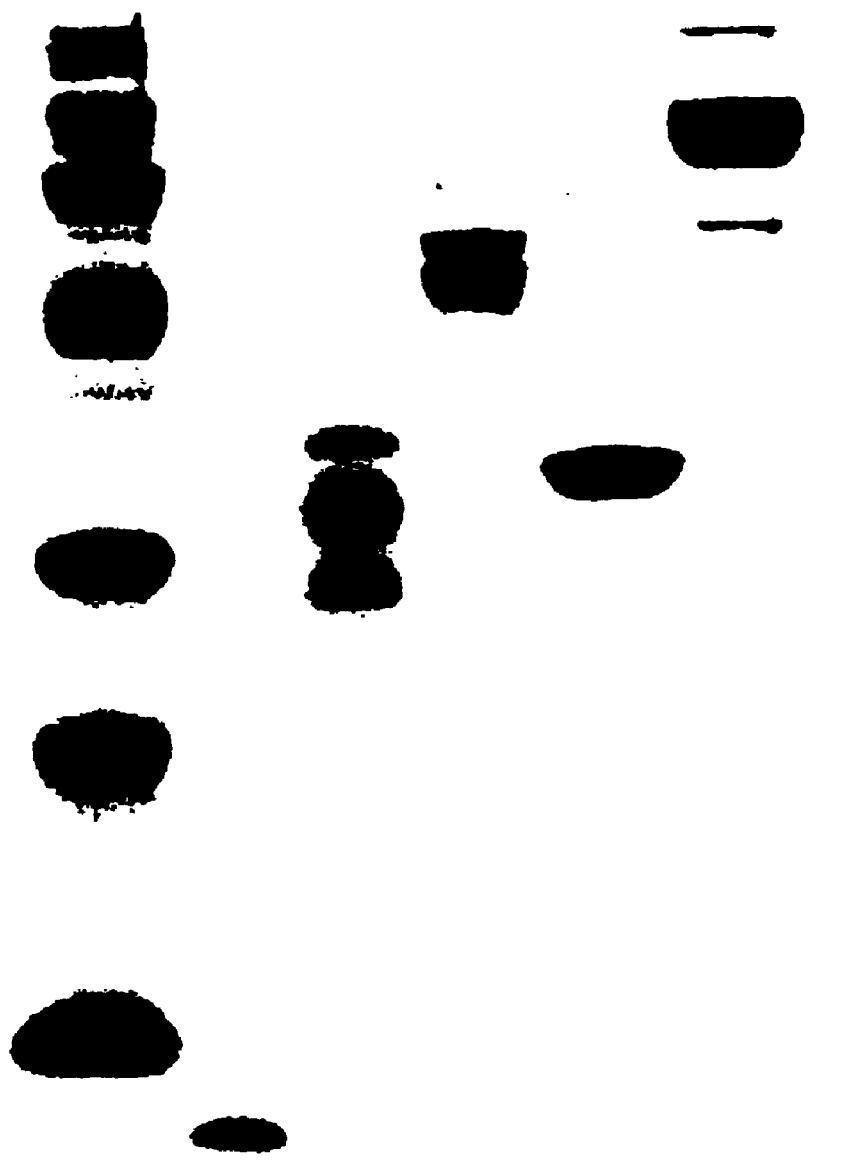
FIG. 3 is a representation of a polyacrylamide gel showing peptide fragments generated by elastase (lanes 2–3) and K-4 protease (lanes 4–6) of glu-plasminogen.

Subsequent to chromatographic separation and removal of trace amounts of uncleaved plasminogen from the 45,000 D peptides using αHPg-247 immunoaffinity chromatography, the purified peptides were analyzed by SDS-PAGE analysis (FIG. 3, lanes 4 and 5). The kringle-containing peptide fragments (kringles 1–3 and kringle 4) generated by elastase cleavage of native glu-plasminogen were also analyzed by SDS-PAGE (FIG. 3, lanes 2 and 3). Kringle 4 (FIG. 3, lane 2) had an approximate molecular weight of 10,000 D. The kringles 1–3 peptide was a mixture of three peptide fragments (FIG. 3, lane 3): kringles 1–3 from plasminogen glycoforms 1 and 2 and an unknown elastase cleavage product. The glu-plasminogen 45,000 D peptides generated by N. nigricollis enzyme proteolysis (FIG. 3, lane 4), and the smaller fragment generated by N. nigricollis treatment of glu-plasminogen (FIG. 3, lane 5) were compared to the elastase cleavage products.

NH$_2$-terminal amino acid sequencing of the 35,000 D peptide generated by N. nigricollis protease cleavage of glu-plasminogen yielded the following amino acid sequence (SEQ ID NO: 5): Asp or Asn-Val-Glu-Thr-Pro-Ser-Glu. Comparison of this sequence to the sequence of fall length glu-plasminogen Robbins, K. C. et al. (1975) J. Biol. Chem. 250: 4044 indicated that the N. nigricollis protease cleaved plasminogen at a single site between Pro$_{451}$ and Asn$_{452}$ separating kringles 1–4 from kringle 5 and the B-chain region. The doublet at 45,000 D represents the kringles 1–4 regions of glu-plasminogen glycoforms 1 and 2 and the 35,000 D peptide consists of kringle 5 and B chain regions.

FIG. 3 is explained in more details as follows:

Plasminogen was cleaved by the N. nigricollis enzyme or by elastase. The peptide fragments were separated using several chromatographic techniques as outlined in the Methods sections. The peptide fragments generated by both enzymes were analyzed by SDS-PAGE, 12–18% under non-reducing conditions. Lane 1: molecular weight standards, lane 2: kringle 4 peptide generated by elastase cleavage of gluplasminogen, lane 3: kringles 1–3 peptide from elastase cleavage, lane 4: 45,000 molecular weight fragments generated by N. nigricollis enzyme treatment of plasminogen, lane 5: 35,000 molecular weight fragment generated by N. nigricollis enzyme and lane 6: plasminogen standard.

As discussed, the present angiogenesis inhibitors have a variety of uses. For example, the following Example 2 shows capacity of preferred angiogenesis inhibitors to disrupt plasminogen-osteonectin binding interactions.

EXAMPLE 2

Figure 4:
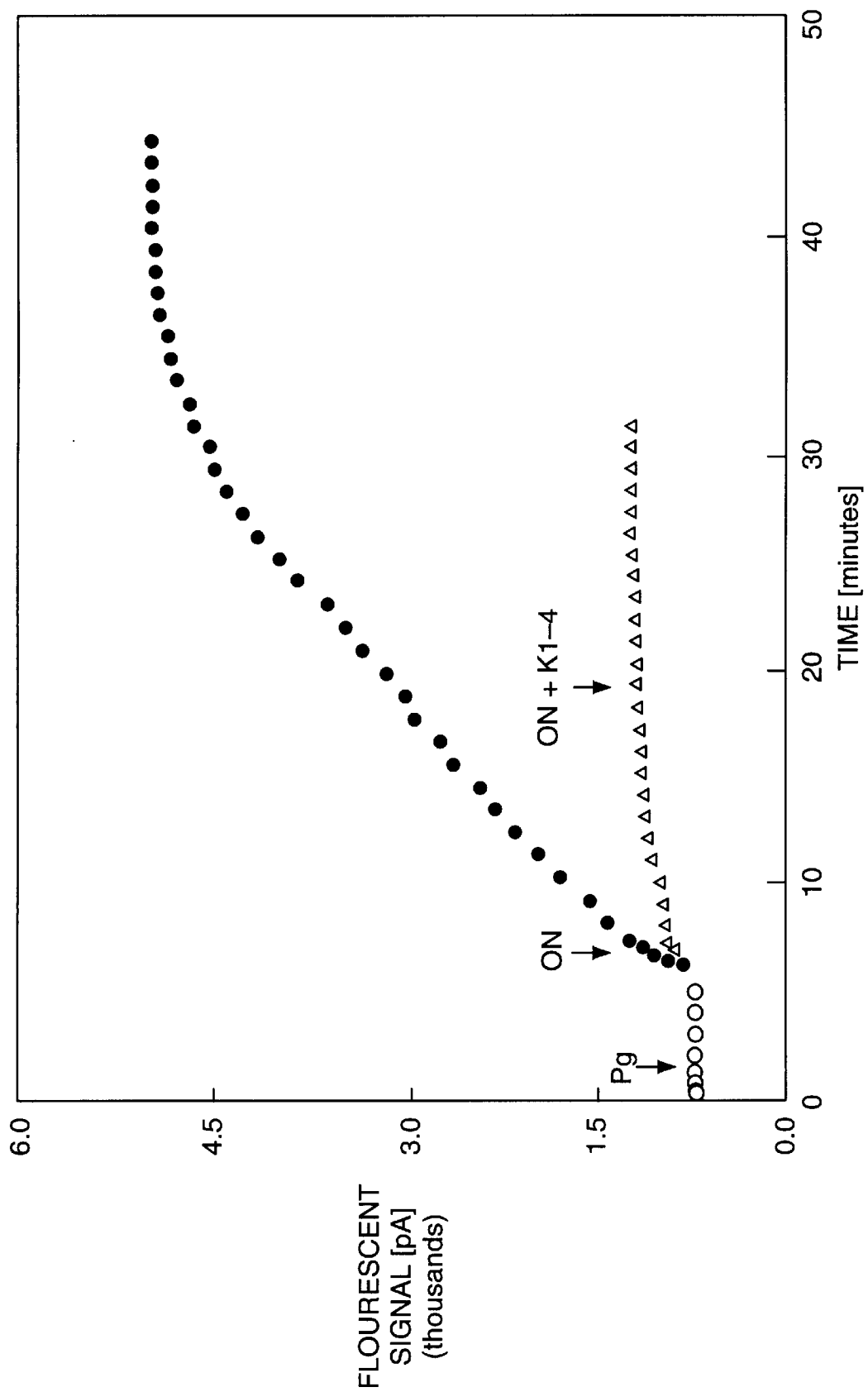
FIG. 4 is a graph showing inhibition of glu-plasminogen-bone osteonectin interaction by the kringles 1–4 measured by TIRFS.

Inhibition of Osteonectin-Plasminogen Interaction by Kringle (K1–4)-Containing Peptides of Plasminogen Bone derived osteonectin, which mediates the binding of plasminogen to a collagen matrix, was utilized for Total Internal Reflection Fluorescence Spectroscopy (TIRFS) binding studies to allow examination of osteonectin-plasminogen interaction in real time under equilibrium conditions. The ability of peptides containing both kringles 1 and 4 or kringle 1 or kringle 4 to inhibit plasminogen-osteonectin interaction was studied using TIRFS. 100 nM fluorescein labeled glu-plasminogen was added to a TIRFS well coated with collagen type V (FIG. 4, open circles). There was no evidence of plasminogen-collagen interaction in the absence of bone osteonectin (FIG. 4, open circles). Subsequent to the addition of plasminogen, 1 µM bone osteonectin was added alone (FIG. 4, closed circles) or in the presence of 2 µM kringles 1–4 peptide (FIG. 4, open triangles). Osteonectin alone mediated the association of plasminogen with the collagen surface while the addition of the kringles 1–4 peptide effectively blocked plasminogen association with osteonectin on the matrix surface.

The effects of the elastase proteolysis products, plasminogen kringles 1–3 and plasminogen kringles 4, on plasminogen-osteonectin interaction were also analyzed by TIRFS (FIG. 5). The addition of a 20-fold molar excess of kringle-containing peptide relative to glu-plasminogen blocked plasminogen-osteonectin interaction.

FIG. 4 is explained more fully as follows:

The figure is a graph showing inhibition of glu-plasminogen-bone osteonectin interaction by the K1–4 peptide measured by TIRFS. The TIRFS sample well was coated with collagen type V. 100 nM fluorescein labeled glu-plasminogen was added to the well (open circle), and a background signal obtained in the absence of osteonectin. 1 $\mu$M bone osteonectin was added alone (closed circle) or in the presence of 2 $\mu$M kringles 1–4 peptide (closed triangle). The fluorescent signal was collected over time until equilibrium, evidence by a plateau in the fluorescent signal, was reached.

Both the kringles 1–3 peptide (FIG. 5A) and the kringle 4 peptide (FIG. 5B) had equivalent effects.

FIGS. 5A and 5B are explained in more detail as follows:

The figures show effects of K1–3 and K4 peptides on glu-plasminogen-bone osteonectin interaction measured by TIRFS. TIRFS wells were coated with collagen type V. 100 nM fluorescein labeled glu-plasminogen was added (open circle) to obtain background fluorescent values. (5A). 1 $\mu$M bone osteonectin was added alone (closed circle) or in the presence of 2 $\mu$M kringles 1–3 peptide (open triangle) and the fluorescent signal was collected over time. (5B). In a separate well containing fluorescein labeled glu-plasminogen, 1 $\mu$M bone osteonectin was added alone (closed circle) or in the presence of 2 $\mu$M kringle 4 peptide (open triangle) and the fluorescent signal was collected over time.

Figure 6:
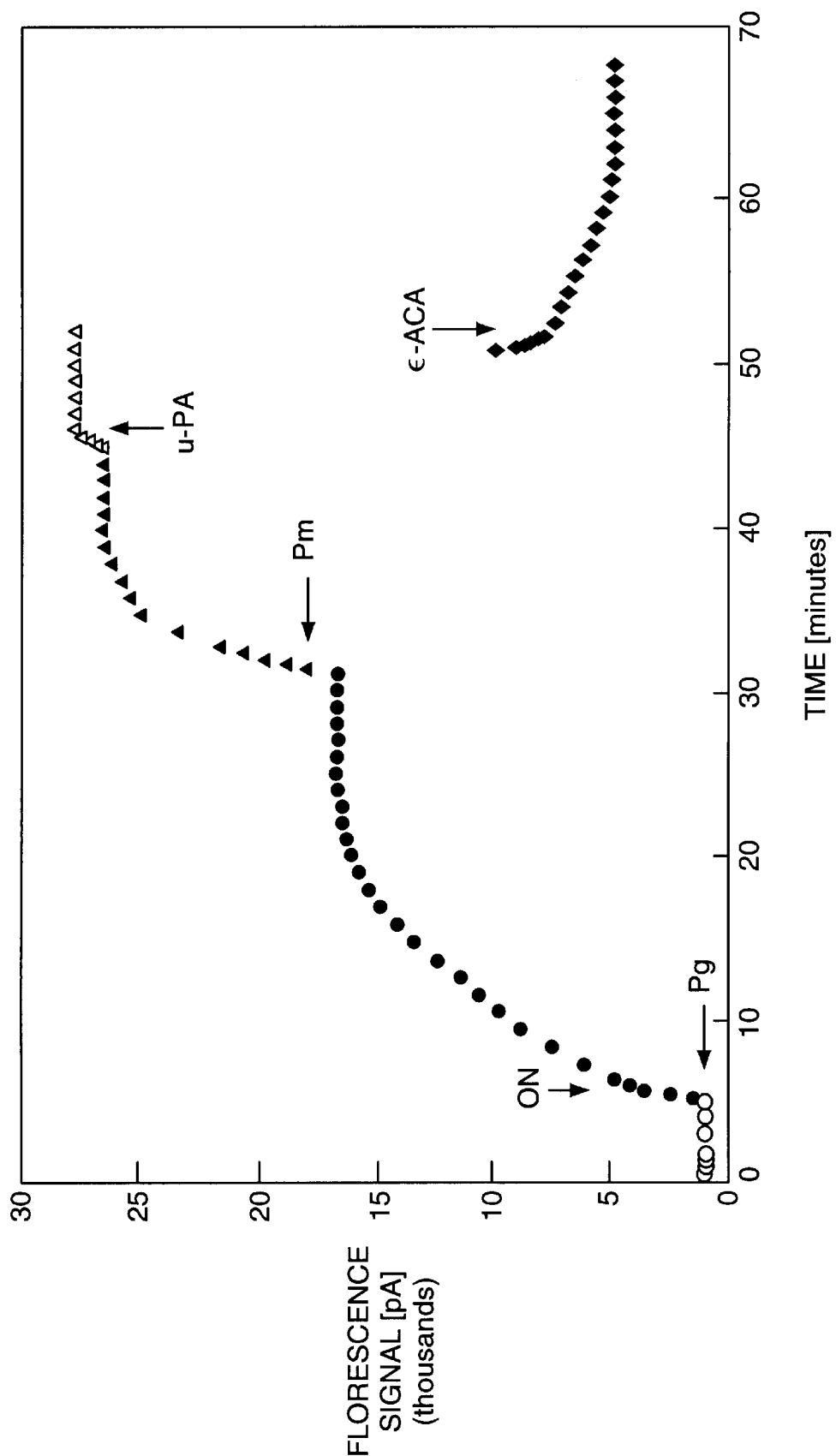
FIG. 6 is a graph showing recombinant plasminogen (S741C)-osteonectin binding interactions.

Recombinant plasminogen (S741C), in which the active site serine was mutated to cysteine, was used to examine the effects of the $NH_2$-terminal peptide, residues 1–77, and plasminogen cleavage during activation to plasmin, on plasminogen/plasmin-osteonectin interactions. Plasminogen (S741C) can be cleaved by plasminogen activators, but will not contain a functional active site preventing feedback proteolysis at residue 77 and removal of the plasminogen $NH_2$-terminal. The lack of an enzymatically active site allows definitive separation of the activation and feedback cleavage events. The plasminogen (S741C) protein also contains a fluorescein probe on the active site cysteine allowing binding events to be monitored by fluorescence detection using TIRFS. 100 nM plasminogen (S741C) was added to a TIRFS well coated with collagen type V (FIG. 6, open circles). No binding was detected in the absence (FIG. 6, open circles), or presence of 2 $\mu$M bone osteonectin (closed circles). The addition of 10 nM plasmin (FIG. 6, closed triangles) resulted in a sharp increase in the fluorescent signal. 10 nM u-PA (FIG. 6, open triangles) caused an initial decrease in the fluorescent signal, consistent with the reduction in plasminogen (S741C) fluorescence upon treatment with plasminogen activators, and a return of the fluorescent signal to the maximum level seen subsequent to plasmin addition as the interaction reached an equilibrium state. 10 mM $\epsilon$-ACA completely reversed the association of plasminogen (S741C) with the surface (FIG. 6, diamonds).

FIG. 6 is explained as follows:

The figure is a graph showing recombinant plasminogen (S741C)-osteonectin binding interactions. 100 nM plasminogen (S741C) was added to TIRFS wells coated with collagen type V (open circle) to obtain a background fluorescent value. 1 $\mu$M bone osteonectin was added (closed circle) followed by the addition of 10 nM plasmin (open triangle). The fluorescent signal was collected over time until and equilibrium value was reached. 10 nM u-PA (open triangle) was added and the signal was allowed to reach an equilibrium value. 10 nM $\epsilon$-ACA (open triangle) was added to the well to block the lysine binding sites on plasminogen.

Figure 7:
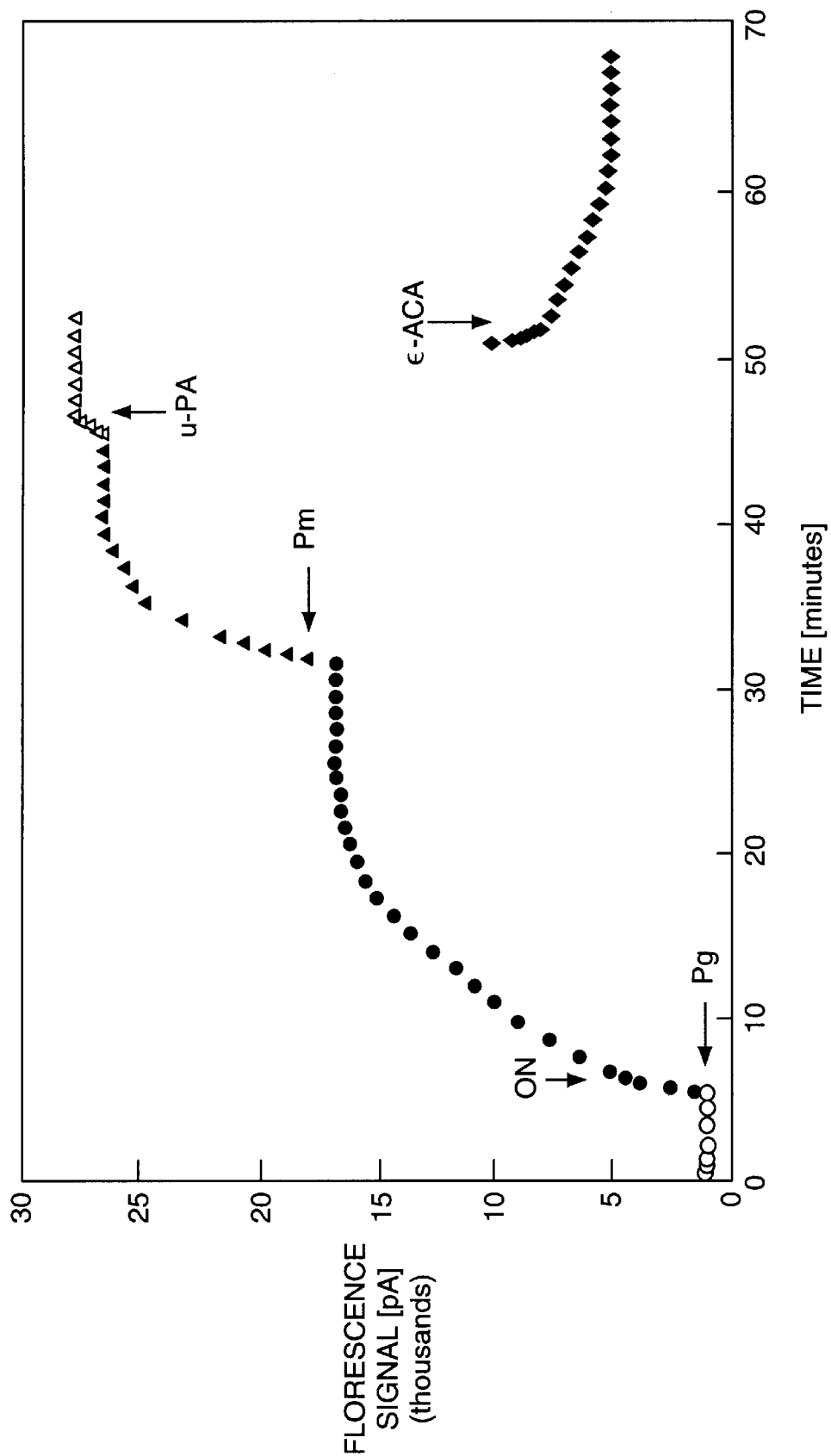
FIG. 7 is a graph showing human glu-plasminogen-osteonectin binding interactions.

The effects of removal of the $NH_2$-terminal peptide on plasminogen-osteonectin interaction were also examined with native, plasma-derived glu-plasminogen (FIG. 7). 100 nM fluorescein labeled glu-plasminogen was added to a TIRFS well coated with collagen type V (FIG. 7, open circles). The addition of 2 $\mu$M bone osteonectin (FIG. 7, closed circles) resulted in a sharp increase in the fluorescent signal. 10 nM plasmin caused a further increase in the fluorescent signal (FIG. 7, closed triangles), with only a small effect on the fluorescent signal seen subsequent to the addition of 10 nM u-PA (FIG. 7, closed triangles). 10 mm $\epsilon$-ACA (FIG. 7, diamonds) completely reversed plasminogen-osteonectin association.

FIG. 7 is explained as follows:

FIG. 7 is a graph showing human glu-plasminogen-osteonectin binding interactions. 100 nM fluorescein labeled glu-plasminogen was added to TIRFS wells coated with collagen type V (open circle) to obtain a background fluorescent value. Addition of 1 $\mu$M bone osteonectin (closed circle) initiated the osteonectin-plasminogen binding event. Subsequent to reaching an equilibrium fluorescent value, 10 nm plasmin (open triangle) and 10 nM u-PA (open triangle) were added in separate steps. 10 mM $\epsilon$-ACA (diamonds) titration reversed the binding event.

The effects of plasminogen confirmational changes and individual and combined plasminogen kringle structures on the osteonectin-plasminogen interaction were examined to determine which of these interactions are important in mediating the osteonectin binding event. These studies utilized a recombinant plasminogen, plasminogen (S741C), in which the active site serine is replaced by cysteine. Use of this recombinant form of plasminogen allows definitive separation of removal of the $NH_2$-terminal peptide and activation of plasminogen by t-PA or urokinase (u-PA). Plasminogen kringle domains were produced by elastase cleavage and with an enzyme from *Naja Nigricollis* venom which generates an intact kringle 1–4 domain.

The following materials and methods were used in the examples as needed.

1. Protein and Peptide Isolation:

Bovine bone osteonectin was extracted (0.5 M EDTA extraction) from finely milled bovine bone femurs and purified using gel filtration and ion-exchange chromatography (Romberg, R. W., et al. (1985) *J. Biol. Chem.* 260: 2728). Bovine bone osteonectin has previously been found to behave in a manner identical to human bone osteonectin (Kelm, R. J., et al. (1994) *J. Biol. Chem.* 269: 30147) Glu-plasminogen glycoforms 1 and 2 were isolated from human plasma using lysine-Sepharose, followed by gel filtration (Castallino, F. J. and Powell, J. R. (1981) *Meth. Enzymol.* 80: 365). Plasmin was generated using the method of Robbins et al. with no addition of leupeptin Robbins, K. C., et al. (1981) *Meth. Enzymol.* 80: 379.

2. Fluorescein Labeling:

A portion of the glu-plasminogen pool was labeled with FITC, 10% adsorbed on Celite (Kelm, R. J., et al. (1994) supra). The fluorophore to protein ratio was approximately 1 mol/mol. The activation rate of labeled plasmingen was compared to unlabeled glu-plasminogen by chromogenic assay using Spectrozyme-PL (Kelm, R. J., et al. (1994) supra). The fluorescein label did not impair plasminogen activation or plasmin activity.

3. Production, Purification and Fluorescein Labeling of Recombinant Plasminogen (S741C):

Baby hamster kidney (BHK-21) cells transfected with the pNUT-Plg(S741C) plasmid (JBC 272:2176) were grown in 500 $cm^2$ triple flasks (Nunc) in Dulbecco's modified medium F-12, supplemented with 5% newborn bovine serum from which plasminogen was removed by passage over lysine-Sepharose. When the cells reached confluence, the cells were washed and the medium was replaced by serum-free Opti-MEM1, supplemented with 50 $\mu$M $ZnCl_2$. Conditioned media were collected at two day intervals, treated with 1 $\mu$M dansyl-Glu-Gly-Arg-chloromethyl ketone, 10 mM Tris-HCl and 1 mM EDTA and were loaded onto lysine-Sepharose. Following a wash with 20 mM $NaH_2PO4/NaHPO_4$,150 mM NaCl, pH 7.4 (PBS), plasminogen (S741C) was eluted with PBS, 10 mM 6-aminohexanoic acid. Plasminogen (S741C) was labeled with 20 mM 5-IAF in N,N'-dimethylformamide for 30 minutes at 26° C. Excess label was removed by chromatography on a DEAE fast flow column (Pharmacia, Uppsala, Sweden). The ratio of fluorescein to protein was typically 0.9 mol/mol (JBC 272:2176).

4. *N. nigricollis* protease isolation:

The procedures described in the Reference Examples 1 and 2 above were generally used except as indicated below:

The protease from *N. nigricollis* venom was purified by gel filtration and ion-exchange chromatography. This protease also specifically cleaves human prothrombin between $Glu_{262}$ and $Asp_{263}$ yielding a peptide fragment analogous to prethrombin 2 (Vijayalakshmi, J. (1994) *Protein Science* 3: 2254). 100 mg of lyophilized venom was added to 2 ml of 0.025 M $NaH_2PO_4/Na_2HPO_4$, 0.10 M NaCl, pH 6.5. The venom solution was applied to a Sephadex G-100 column equilibrated in the same buffer. The proteins eluted from the column were combined in several pools based on the elution profile and assayed for ability to cleave plasminogen. 10 $\mu$g of glu-plasminogen was incubated with approximately 5 $\mu$g of protein from each pool (assuming an extinction coefficient $E^1\%_{cm,280nm}$=10.0 for the mixtures of proteins in the pools). The incubation was carried out at 37° C. for 3 hours. The samples were analyzed by SDS-PAGE under non-reducing and reducing conditions (Laemmli, U. K. (1970) *Nature* 227: 680) to determine which of the protein pools contained the appropriate protease. The protease-containing pools were combined and dialyzed versus 0.025 M $NaH_2PO_4/Na_2HPO_4$, pH 6.5 before being applied to a Sulfopropyl Sephadex C50 column equilibrated in the same buffer. After washing with the above buffer, protein fractions were eluted with a step gradient: 1) 0.05 M $NaH_2PO_4/Na_2HPO_4$, pH 6.5, 2) 0.10 M $NaH_2 PO_4/Na_2HPO_4$, pH 6.5 and 3)0.25 M $NaH_2PO_4/Na_2HPO_4$, pH 6.5. The protein fractions were pooled based on the elution profile and assayed for the ability to cleave plasminogen. The desired protease was located in the final elution. The *N. nigricollis* protease was analyzed by SDS-PAGE under reducing and non-reducing conditions Laemmli, U. K. (1970) supra. The protein had a molecular weight of approximately 10,000 with several higher molecular weight components when evaluated by SDS-PAGE analysis.

5. Isolation of Peptide Fragments of Plasminogen

Fragments of human glu-plasminogen were produced by proteolytic cleavage. Kringles 1–3 (residues 79–353) and kringle 4 (residues 354–439) were isolated following elastase digestion as described by Powell and Castellino Powell, J. R. and Castallino, F. J. (1980) *J. Biol. Chem.* 255: 5329. Other peptide fragments were isolated following treatment of glu-plasminogen with the *N. nigricollis* protease. Glu-plasminogen in PBS, 2 mM $CaCl_2$ at a concentration of 1 mg/ml was incubated with 10 $\mu$g/ml purified *N. nigricollis* protease for 1 h at 37° C. The reaction was quenched by the addition of 5 mM EDTA. The protein mixture was applied to a lysine-Sepharose column equilibrated in PBS. One fragment was present in the flow-through of the column. Other peptides were eluted by the addition of PBS, 50 mM $\epsilon$-amino caproic acid ($\epsilon$-ACA). The peptides eluted from the lysine-Sepharose column were further purified by immunoaffinity chromatography using $\alpha$HPg-247-Sepharose. $\alpha$HPg-247 is a monoclonal antibody that recognizes the kringle 5-B chain region of plasminogen (Church, W. R. and Messier, T. L. (1991) *Hybridoma* 10: 659). Immunoaffinity chromatography also removed any traces of uncleaved plasminogen from the lysine-binding peptides.

6. $NH_2$-terminal Amino Acid Sequencing

The NH2 -terminal sequence of the 35,000 molecular weight peptide (which was not retained on lysine-Sepharose) generated by *N. nigricollis* protease cleavage of plasminogen was obtained by automated Edman degradation using an Applied Biosystems 475A Protein Sequencing System (Applied Biosystems, Foster City, Calif.). The sample (100 pmoles) was dialyzed versus 50 mM $NH_4HCO_3$ and lyophilized. The lyophilized peptide was resuspended in 10% acetic acid and applied to the sequencer.

7. Total Internal Reflection Fluorescence Spectroscopy (TIRFS) Equilibrium Binding Studies The initiation of many physiologically relevant reactions is dependent on the binding of proteins from solution to a surface such as an extracellular matrix or a cell membrane. TIRFS measures these surface dependent binding events in real time under equilibrium conditions (Kelm, R. J., et al. (1994) supra; Swords, N. A. and Mann, K. G. (1993) *Arterioscl. Thromb.* 13: 1602; Liebmann, L. W., et al. (1991) *Rev. Sci. Instrum.* 62: 2083). A 5W argon ion laser (Spectra Physics 2025-05) provided the excitation light source. The light power was regulated with an acoustic-optic modulator (Newport EOS) and a mechanical chopper (Stanford Research Corp.)

The beam was focused through the 73 ° angle in the TIR element generating an elliptical reflection spot centered over the light collection optics. An electronic shutter with a beam trap (Vincent Associates) blocked the incident beam between data readings preventing sample heating and photobleaching of the fluorophore. The TIR element was mounted on a Zeiss inverted microscope equipped with a photomultiplier tube (Hanmuamatsu) at the top of the optical column. The experimental parameters were controlled through a dedicated PC (Kelm, R. J., et al. (1994) supra; Liebmann, L. W., et al. (1991) *Rev. Sci. Instrum.* 62: 2083). For binding experiments with fluorescein labeled glu-plasminogen, an excitation wavelength of 488 nm and a 520 nm cutoff filter were used to select for fluorescein excitation and emission. Binding experiments were performed at 25° C. under stirred conditions to provide continuous mixing of reagents in the well. The signals from 10 second excitation pulses were collected at increasing time intervals with a final interval of 1 minute.

TIRFS sample wells were cleaned in an air plasma cleaner. The TIRFS wells were coated with human collagen type V (Kelm, R. J., et al. (1994) supra). 100 $\mu$l of a 10 $\mu$g/ml solution of collagen in 0.05M $Na_2CO_3/NaHCO_3$, pH 9.7 was placed in each well and incubated for 18 h at 4° C. The wells were washed three times with 0.02M Tris, 0.15M NaCl, 0.002M $CaCl_2$, 0.05% v/v Tween 20, pH 7.4 (TBS/Tween/$CaCl_2$). The wells were incubated for 1 h with 300 $\mu$l of the same buffer. The buffer was removed and fresh buffer was added. 100 nM FITC-glu-plasminogen was added to the wells and a background, nonspecific fluorescence value was obtained. (No interaction of plasminogen with the collagen matrix was detected in the absence of bone osteonectin.) 1 $\mu$M bone osteonectin alone, or preincubated with 2 $\mu$M kringles 1–4, Kringles 1–3 or kringle 4 peptides was added to the plasminogen-containing well. The fluorescence values were collected over time to monitor the collagen-osteonectin-plasminogen-peptide binding events on the surface. The effect of the $NH_2$ terminal, residues 1–77, of plasminogen on plasminogen-osteonectin interaction was also examined using TURFS. 100 nM recombinant plasminogen (S741C) which contained a fluorescein probe coupled to cysteine 741 (Horrevoets, A., et al. (1994) *Fibrinolysis* 8: 1) was added to a TIRFS well coated with collagen type V.

A background fluorescent signal was collected prior to the addition of 2 µM bone osteonectin. Subsequent to the addition of osteonectin, 10 nM low molecular weight urokinase (u-PA) was added. u-PA will cleave the recombinant plasminogen at $Arg_{560}$–$Val_{561}$ but no active site will be generated due to the mutation. Activation of the fluorescein labeled plasminogen S741C results in a 25% decrease in the fluorescent signal Horrevoets, A., et al. (1994) *Fibrinolysis* 8: 1. In a separate experiment, 100 nM plasminogen S741C was added to a TIRFS well coated with collagen type V. Sequential additions of 2 µM bone osteonectin, 10 nm plasmin, 10 nM u-PA and 10 mM ∈-amino caproic acid (∈-ACA) were made allowing the fluorescent signal to reach equilibrium (evidenced by a plateau in the signal) between each addition. The same experiment was conducted using plasma-derived glu-plasminogen as well.

7. Materials

*N. nigricollis* venom (lot #103F-0018) and human placental collagen type V were purchased from Sigma (St. Louis, Mo.). Fluorescein-5-isothiocyanate (FITC), 10% absorbed on Celite, and 5-iodoacetamidofluorescein (5-IAF) were obtained from Molecular Probes (Eugene, Oreg.). Elastase was purchased from Worthington Biochemical (Freehold, N.J.). Chromogenic substrates for plasmin, Spectrozyme-PL and S2251, were from American Diagnostica (Greenwich, Conn.), and Kabi Pharmacia (Franklin, Ohio), respectively. Dansyl-Glu-Gly-Arg-chloromethyl ketone was obtained from Helena laboratories (Mississauga, Ontario, Canada). Dulbecco's modified Eagle's medium:nutrient mixture F-12 (1:1), Opti-MEM 1 and newborn bovine serum were from Life Technologies, Inc. Recombinant low molecular weight urokinase was kindly donated by Dr. Jack Henkin (Abbott Laboratories, Abbott Park, Ill.).

The examples show that *N. nigricollis* venom can cleave native glu-plasminogen at a single site. The *N. nigricollis* enzyme cleaved plasminogen to yield two peptide fragments: intact kringles 1–4 (residues 1-451) and kringle 5-B chain (residues 452–790). Cleavage of plasminogen by the *N. nigricollis* enzyme did not generate an enzymatically active plasma species.

Example 2 illustrates ability of the intact kringles 1–4 peptide to compete with full length glu-plasminogen for binding sites on bone osteonectin analyzed under equilibrium conditions using TIRFS. The kringles 1–4 peptide was able to block the association of glu-plasminogen with bone osteonectin localized on a collagen matrix. The kringles 1–3 and kringle 4 peptides generated by elastase cleavage of glu-plasminogen were also found to inhibit full length glu-plasminogen association with bone osteonectin on the collagen matrix. The osteonectin-plasminogen interaction appears to be dependent on the lysine binding sites associated with plasminogen, specifically, the high affinity sites on the kringle 1 domain and the lower affinity sites on the kringle 4, and possibly the kringle 3, domain.

Recombinant plasminogen (S741C) was used to study the effects of plasminogen activation and removal of the $NH_2$-terminal peptide of plasminogen on osteonectin-plasminogen interaction. The active site serine in plasminogen (S741C) is replaced by cysteine allowing the molecule to be cleaved by plasminogen activators, but preventing expression of a functional active site (Horrevoets, A., et al. (1994) supra). Studies with plasminogen (S741C) allow the activation event to be clearly distinguished from plasmin feedback cleavage which removes the $NH_2$-terminal The presence of the $NH_2$-terminal appeared to completely block the binding of plasminogen (S741C) to bone osteonectin on a collagen matrix. Removal of the peptide by plasmin proteolysis allowed $Lys_{78}$-plasminogen (S741C) to bind to bone osteonectin. Subsequent cleavage of the recombinant plasminogen molecule by u-PA had no discernible effect on the plasminogen-osteonectin binding interaction. Titration of the $Lys_{78}$-plasminogen (S741C)-osteonectin complexes with the lysine analogue ∈-ACA completely reversed plasminogen/plasmin association with bone osteonectin on the collagen matrix. The binding of the recombinant plasminogen (S741C) molecule to osteonectin appears to be dependent on the plasminogen conformational change which occurs as a result of removal of the $NH_2$-terminus and is also dependent on the lysine binding sites present on the plasminogen molecule.

Similar effects were obtained with plasma-derived glu-plasminogen. However, significant interaction between plasma glu-plasminogen and bone osteonectin was detected before enzymatic removal of the plasminogen $NH_2$-terminal. This may be due to the presence of $Lys_{78}$-plasminogen in the material isolated from human plasma. Enzymatic removal of the $NH_2$-terminal did significantly increase plasminogen association with the surface bound osteonectin and subsequent activation of the $Lys_{78}$-plasminogen with u-PA had only a small effect on binding. The binding event was also mediated by the lysine binding sites as titration with ∈-ACA completely reversed plasminogen/plasmin association with bone osteonectin.

The kringle 1 and 4 regions of plasminogen were identified as important regulators of the interaction between osteonectin and plasminogen. To further analyze the importance of these regions, kringles 1–3 and kringle 4 fragments were made using the enzyme elastase and also cleaved plasminogen with the enzyme isolated from *Naja Nigricollis* venom. The K-4 protease cleaved plasminogen at Proline 451-Asparagine 452 generating an intact kringles 1–4 fragment (See FIG. 1). (The doublet present in FIG. 2A at the K 1–4 band is due to the two glycoforms of plasminogen.)

The invention has been described in detail with reference to preferred embodiments thereof. However, it will be appreciated that those skilled in the art, upon consideration of this disclosure, may make modification and improvements within the spirit and scope of the invention as set forth in the following claims.

What is claimed is:

1. A method for making an isolated angiogenesis inhibitor having a molecular weight of between about 40 kDa to 50 kDa and having an amino acid sequence having at least about 85% identity to that of the amino acid sequence shown in SEQ ID NO. 1 or SEQ ID NO. 3, the method comprising:

a) contacting plasminogen with an amount of Kringle-4 protease from *Naja Nigricollis Nigricollis* sufficient to cleave the plasminogen into fragments comprising fragments having a molecular weight of between about 50 kDa to 70 kDa, b) contacting the fragments with an amount of a second protease sufficient to cleave the fragments at between about the first 50 and 80 amino acids of the plasminogen; and c) isolating the angiogenesis inhibitor from the plasminogen fragments, wherein the second protease is elastase or plasmin.

2. The method of claim 1, wherein the plasminogen is glycosylated.

3. The method of claim 1, wherein between steps a) and b) the method further comprises eluting the cleaved plasminogen fragments from a first chromatographic implementation.

4. The method of claim 3, wherein the method further comprises purifying the eluted fragments on a second chromatographic implementation capable of specifically binding the fragments having the molecular weight of between about 50 kDa to 70 kDa.

5. The method of claim 4, wherein the first chromatographic implementation comprises lysine-sepharose and the second chromatographic implementation comprises an anti-plasminogen antibody or antigen binding fragment thereof.

6. The method of claim 5, wherein the anti-plasminogen antibody is capable of specifically binding the kringle B chain region of human plasminogen.

7. The method of claim 6, wherein the second protease is plasmin and the plasminogen fragments are cleaved at or about amino acid 77 of SEQ ID NO. 2 or amino acid 78 of SEQ ID NO. 3.

\* \* \* \* \*

UNITED STATES PATENT AND TRADEMARK OFFICE
CERTIFICATE OF CORRECTION

PATENT NO. : 6,365,364 B1
DATED : April 2, 2002
INVENTOR(S) : Kenneth G. Mann and Nancy Swords Jenny It is certified that error appears in the above-identified patent and that said Letters Patent is hereby corrected as shown below:

Column 1,
Line 8, please insert the following:

-- STATEMENT OF GOVERNMENT SUPPORT

Funding for this invention was provided in part by the Government of the United States of America, through Grant No. HL34575, by the National Institutes of Health. The Government has certain rights in this invention. --

Signed and Sealed this

Twenty-second Day of March, 2005

JON W. DUDAS
*Director of the United States Patent and Trademark Office*

SEQUENCE LISTING

<160> NUMBER OF SEQ ID NOS: 5

<210> SEQ ID NO 1
<211> LENGTH: 451
<212> TYPE: PRT
<213> ORGANISM: Homo sapiens
<220> FEATURE:
<223> OTHER INFORMATION: plasminogen fragment
<220> FEATURE:
<221> NAME/KEY: MOD_RES
<222> LOCATION: (53)
<223> OTHER INFORMATION: Xaa = Gln or Glu
<220> FEATURE:
<221> NAME/KEY: MOD_RES
<222> LOCATION: (341)
<223> OTHER INFORMATION: Xaa = Gln or Glu

<400> SEQUENCE: 1

```
Glu Pro Leu Asp Asp Tyr Val Asn Thr Gln Gly Ala Ser Leu Phe Ser
 1               5                  10                  15

Val Thr Lys Lys Gln Leu Gly Ala Gly Ser Ile Glu Glu Cys Ala Ala
             20                  25                  30

Lys Cys Glu Glu Asp Glu Glu Phe Thr Cys Arg Ala Phe Gln Tyr His
         35                  40                  45

Ser Lys Glu Gln Xaa Cys Val Ile Met Ala Glu Asn Arg Lys Ser Ser
     50                  55                  60

Ile Ile Arg Met Arg Asp Val Val Leu Phe Glu Lys Lys Val Tyr Leu
 65                  70                  75                  80

Ser Glu Cys Lys Thr Gly Asn Gly Lys Asn Tyr Arg Gly Thr Met Ser
                 85                  90                  95

Lys Thr Lys Asn Gly Ile Thr Cys Gln Lys Trp Ser Ser Thr Ser Pro
            100                 105                 110

His Arg Pro Arg Phe Ser Pro Ala Thr His Pro Ser Glu Gly Leu Glu
        115                 120                 125

Glu Asn Tyr Cys Arg Asn Pro Asp Asn Asp Pro Gln Gly Pro Trp Cys
    130                 135                 140

Tyr Thr Thr Asp Pro Glu Lys Arg Tyr Asp Tyr Cys Asp Ile Leu Glu
145                 150                 155                 160

Cys Glu Glu Glu Cys Met His Cys Ser Gly Glu Asn Tyr Asp Gly Lys
                165                 170                 175

Ile Ser Lys Thr Met Ser Gly Leu Glu Cys Gln Ala Trp Asp Ser Gln
            180                 185                 190

Ser Pro His Ala His Gly Tyr Ile Pro Ser Lys Phe Pro Asn Lys Asn
        195                 200                 205

Leu Lys Lys Asn Tyr Cys Arg Asn Pro Asp Arg Glu Leu Arg Pro Trp
    210                 215                 220

Cys Phe Thr Thr Asp Pro Asn Lys Arg Trp Glu Leu Cys Asp Ile Pro
225                 230                 235                 240

Arg Cys Thr Thr Pro Pro Pro Ser Ser Gly Pro Thr Tyr Gln Cys Leu
                245                 250                 255

Lys Gly Thr Gly Glu Asn Tyr Arg Gly Asn Val Ala Val Thr Val Ser
            260                 265                 270

Gly His Thr Cys Gln His Trp Ser Ala Gln Thr Pro His Thr His Asn
        275                 280                 285

Arg Thr Pro Glu Asn Phe Pro Cys Lys Asn Leu Asp Glu Asn Tyr Cys
    290                 295                 300
```

```
Arg Asn Pro Asp Gly Lys Arg Ala Pro Trp Cys His Thr Thr Asn Ser
305                 310                 315                 320

Gln Val Arg Trp Glu Tyr Cys Lys Ile Pro Ser Cys Asp Ser Ser Pro
            325                 330                 335

Val Ser Thr Glu Xaa Leu Ala Pro Thr Ala Pro Pro Glu Leu Thr Pro
            340                 345                 350

Val Val Gln Asp Cys Tyr His Gly Asp Gly Gln Ser Tyr Arg Gly Thr
            355                 360                 365

Ser Ser Thr Thr Thr Thr Gly Lys Lys Cys Gln Ser Trp Ser Ser Met
        370                 375                 380

Thr Pro His Arg His Gln Lys Thr Pro Glu Asn Tyr Pro Asn Ala Gly
385                 390                 395                 400

Leu Thr Met Asn Tyr Cys Arg Asn Pro Asp Ala Asp Lys Gly Pro Trp
                405                 410                 415

Cys Phe Thr Thr Asp Pro Ser Val Arg Trp Glu Tyr Cys Asn Leu Lys
                420                 425                 430

Lys Cys Ser Gly Thr Glu Ala Ser Val Val Ala Pro Pro Pro Val Val
            435                 440                 445

Leu Leu Pro
450

<210> SEQ ID NO 2
<211> LENGTH: 375
<212> TYPE: PRT
<213> ORGANISM: Homo sapiens
<220> FEATURE:
<223> OTHER INFORMATION: angiogenesis inhibitor
<220> FEATURE:
<221> NAME/KEY: MOD_RES
<222> LOCATION: (265)
<223> OTHER INFORMATION: Xaa = Gln or Glu

<400> SEQUENCE: 2

Lys Val Tyr Leu Ser Glu Cys Lys Thr Gly Asn Gly Lys Asn Tyr Arg
  1               5                  10                  15

Gly Thr Met Ser Lys Thr Lys Asn Gly Ile Thr Cys Gln Lys Trp Ser
                20                  25                  30

Ser Thr Ser Pro His Arg Pro Arg Phe Ser Pro Ala Thr His Pro Ser
            35                  40                  45

Glu Gly Leu Glu Glu Asn Tyr Cys Arg Asn Pro Asp Asn Asp Pro Gln
    50                  55                  60

Gly Pro Trp Cys Tyr Thr Thr Asp Pro Glu Lys Arg Tyr Asp Tyr Cys
65                  70                  75                  80

Asp Ile Leu Glu Cys Glu Glu Cys Met His Cys Ser Gly Glu Asn
                85                  90                  95

Tyr Asp Gly Lys Ile Ser Lys Thr Met Ser Gly Leu Glu Cys Gln Ala
                100                 105                 110

Trp Asp Ser Gln Ser Pro His Ala His Gly Tyr Ile Pro Ser Lys Phe
            115                 120                 125

Pro Asn Lys Asn Leu Lys Lys Asn Tyr Cys Arg Asn Pro Asp Arg Glu
130                 135                 140

Leu Arg Pro Trp Cys Phe Thr Thr Asp Pro Asn Lys Arg Trp Glu Leu
145                 150                 155                 160

Cys Asp Ile Pro Arg Cys Thr Thr Pro Pro Ser Ser Gly Pro Thr
                165                 170                 175

Tyr Gln Cys Leu Lys Gly Thr Gly Glu Asn Tyr Arg Gly Asn Val Ala
                180                 185                 190
```

-continued

```
Val Thr Val Ser Gly His Thr Cys Gln His Trp Ser Ala Gln Thr Pro
            195                 200                 205

His Thr His Asn Arg Thr Pro Glu Asn Phe Pro Cys Lys Asn Leu Asp
        210                 215                 220

Glu Asn Tyr Cys Arg Asn Pro Asp Gly Lys Arg Ala Pro Trp Cys His
225                 230                 235                 240

Thr Thr Asn Ser Gln Val Arg Trp Glu Tyr Cys Lys Ile Pro Ser Cys
                245                 250                 255

Asp Ser Ser Pro Val Ser Thr Glu Xaa Leu Ala Pro Thr Ala Pro Pro
            260                 265                 270

Glu Leu Thr Pro Val Val Gln Asp Cys Tyr His Gly Asp Gly Gln Ser
        275                 280                 285

Tyr Arg Gly Thr Ser Ser Thr Thr Thr Gly Lys Lys Cys Gln Ser
    290                 295                 300

Trp Ser Ser Met Thr Pro His Arg His Gln Lys Thr Pro Glu Asn Tyr
305                 310                 315                 320

Pro Asn Ala Gly Leu Thr Met Asn Tyr Cys Arg Asn Pro Asp Ala Asp
                325                 330                 335

Lys Gly Pro Trp Cys Phe Thr Thr Asp Pro Ser Val Arg Trp Glu Tyr
            340                 345                 350

Cys Asn Leu Lys Lys Cys Ser Gly Thr Glu Ala Ser Val Val Ala Pro
        355                 360                 365

Pro Pro Val Val Leu Leu Pro
    370                 375

<210> SEQ ID NO 3
<211> LENGTH: 374
<212> TYPE: PRT
<213> ORGANISM: Homo sapiens
<220> FEATURE:
<223> OTHER INFORMATION: angiogenesis inhibitor
<220> FEATURE:
<221> NAME/KEY: MOD_RES
<222> LOCATION: (264)
<223> OTHER INFORMATION: Xaa = Gln or Glu

<400> SEQUENCE: 3

Val Tyr Leu Ser Glu Cys Lys Thr Gly Asn Gly Lys Asn Tyr Arg Gly
  1               5                  10                  15

Thr Met Ser Lys Thr Lys Asn Gly Ile Thr Cys Gln Lys Trp Ser Ser
                20                  25                  30

Thr Ser Pro His Arg Pro Arg Phe Ser Pro Ala Thr His Pro Ser Glu
            35                  40                  45

Gly Leu Glu Glu Asn Tyr Cys Arg Asn Pro Asp Asn Asp Pro Gln Gly
        50                  55                  60

Pro Trp Cys Tyr Thr Thr Asp Pro Glu Lys Arg Tyr Asp Tyr Cys Asp
65                  70                  75                  80

Ile Leu Glu Cys Glu Glu Glu Cys Met His Cys Ser Gly Glu Asn Tyr
                85                  90                  95

Asp Gly Lys Ile Ser Lys Thr Met Ser Gly Leu Glu Cys Gln Ala Trp
            100                 105                 110

Asp Ser Gln Ser Pro His Ala His Gly Tyr Ile Pro Ser Lys Phe Pro
        115                 120                 125

Asn Lys Asn Leu Lys Lys Asn Tyr Cys Arg Asn Pro Asp Arg Glu Leu
    130                 135                 140

Arg Pro Trp Cys Phe Thr Thr Asp Pro Asn Lys Arg Trp Glu Leu Cys
145                 150                 155                 160
```

```
Asp Ile Pro Arg Cys Thr Thr Pro Pro Ser Ser Gly Pro Thr Tyr
                165                 170                 175

Gln Cys Leu Lys Gly Thr Gly Glu Asn Tyr Arg Gly Asn Val Ala Val
                180                 185                 190

Thr Val Ser Gly His Thr Cys Gln His Trp Ser Ala Gln Thr Pro His
            195                 200                 205

Thr His Asn Arg Thr Pro Glu Asn Phe Pro Cys Lys Asn Leu Asp Glu
        210                 215                 220

Asn Tyr Cys Arg Asn Pro Asp Gly Lys Arg Ala Pro Trp Cys His Thr
225                 230                 235                 240

Thr Asn Ser Gln Val Arg Trp Glu Tyr Cys Lys Ile Pro Ser Cys Asp
                245                 250                 255

Ser Ser Pro Val Ser Thr Glu Xaa Leu Ala Pro Thr Ala Pro Pro Glu
                260                 265                 270

Leu Thr Pro Val Val Gln Asp Cys Tyr His Gly Asp Gly Gln Ser Tyr
            275                 280                 285

Arg Gly Thr Ser Ser Thr Thr Thr Thr Gly Lys Lys Cys Gln Ser Trp
        290                 295                 300

Ser Ser Met Thr Pro His Arg His Gln Lys Thr Pro Glu Asn Tyr Pro
305                 310                 315                 320

Asn Ala Gly Leu Thr Met Asn Tyr Cys Arg Asn Pro Asp Ala Asp Lys
                325                 330                 335

Gly Pro Trp Cys Phe Thr Thr Asp Pro Ser Val Arg Trp Glu Tyr Cys
            340                 345                 350

Asn Leu Lys Lys Cys Ser Gly Thr Glu Ala Ser Val Val Ala Pro Pro
            355                 360                 365

Pro Val Val Leu Pro
    370

<210> SEQ ID NO 4
<211> LENGTH: 452
<212> TYPE: PRT
<213> ORGANISM: Homo sapiens
<220> FEATURE:
<223> OTHER INFORMATION: plasminogen fragment
<220> FEATURE:
<221> NAME/KEY: MOD_RES
<222> LOCATION: (53)
<223> OTHER INFORMATION: Xaa = Gln or Glu
<220> FEATURE:
<221> NAME/KEY: MOD_RES
<222> LOCATION: (342)
<223> OTHER INFORMATION: Xaa = Gln or Glu

<400> SEQUENCE: 4

Glu Pro Leu Asp Asp Tyr Val Asn Thr Gln Gly Ala Ser Leu Phe Ser
 1               5                  10                  15

Val Thr Lys Lys Gln Leu Gly Ala Gly Ser Ile Glu Glu Cys Ala Ala
                20                  25                  30

Lys Cys Glu Glu Asp Glu Glu Phe Thr Cys Arg Ala Phe Gln Tyr His
            35                  40                  45

Ser Lys Glu Gln Xaa Cys Val Ile Met Ala Glu Asn Arg Lys Ser Ser
        50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95
```

-continued

```
Ser Lys Thr Lys Asn Gly Ile Thr Cys Gln Lys Trp Ser Ser Thr Ser
            100                 105                 110
Pro His Arg Pro Arg Phe Ser Pro Ala Thr His Pro Ser Glu Gly Leu
        115                 120                 125
Glu Glu Asn Tyr Cys Arg Asn Pro Asp Asn Asp Pro Gln Gly Pro Trp
    130                 135                 140
Cys Tyr Thr Thr Asp Pro Glu Lys Arg Tyr Asp Tyr Cys Asp Ile Leu
145                 150                 155                 160
Glu Cys Glu Glu Glu Cys Met His Cys Ser Gly Glu Asn Tyr Asp Gly
                165                 170                 175
Lys Ile Ser Lys Thr Met Ser Gly Leu Glu Cys Gln Ala Trp Asp Ser
            180                 185                 190
Gln Ser Pro His Ala His Gly Tyr Ile Pro Ser Lys Phe Pro Asn Lys
        195                 200                 205
Asn Leu Lys Lys Asn Tyr Cys Arg Asn Pro Asp Arg Glu Leu Arg Pro
    210                 215                 220
Trp Cys Phe Thr Thr Asp Pro Asn Lys Arg Trp Glu Leu Cys Asp Ile
225                 230                 235                 240
Pro Arg Cys Thr Thr Pro Pro Ser Ser Gly Pro Thr Tyr Gln Cys
                245                 250                 255
Leu Lys Gly Thr Gly Glu Asn Tyr Arg Gly Asn Val Ala Val Thr Val
            260                 265                 270
Ser Gly His Thr Cys Gln His Trp Ser Ala Gln Thr Pro His Thr His
        275                 280                 285
Asn Arg Thr Pro Glu Asn Phe Pro Cys Lys Asn Leu Asp Glu Asn Tyr
    290                 295                 300
Cys Arg Asn Pro Asp Gly Lys Arg Ala Pro Trp Cys His Thr Thr Asn
305                 310                 315                 320
Ser Gln Val Arg Trp Glu Tyr Cys Lys Ile Pro Ser Cys Asp Ser Ser
                325                 330                 335
Pro Val Ser Thr Glu Xaa Leu Ala Pro Thr Ala Pro Pro Glu Leu Thr
            340                 345                 350
Pro Val Val Gln Asp Cys Tyr His Gly Asp Gly Gln Ser Tyr Arg Gly
        355                 360                 365
Thr Ser Ser Thr Thr Thr Thr Gly Lys Lys Cys Gln Ser Trp Ser Ser
    370                 375                 380
Met Thr Pro His Arg His Gln Lys Thr Pro Glu Asn Tyr Pro Asn Ala
385                 390                 395                 400
Gly Leu Thr Met Asn Tyr Cys Arg Asn Pro Asp Ala Asp Lys Gly Pro
                405                 410                 415
Trp Cys Phe Thr Thr Asp Pro Ser Val Arg Trp Glu Tyr Cys Asn Leu
            420                 425                 430
Lys Lys Cys Ser Gly Thr Glu Ala Ser Val Val Ala Pro Pro Pro Val
        435                 440                 445
Val Leu Leu Pro
    450

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: peptide
      fragment generated by N. nigricollis protease cleavage of
      glu-plasminogen
<220> FEATUR

```
<221> NAME/KEY: MOD_RES
<222> LOCATION: (1)
<223> OTHER INFORMATION: Xaa = Asp or Asn

<400> SEQUENCE: 5

Xaa Val Glu Thr Pro Ser Glu
 1                   5
```